US006949629B2

(12) United States Patent
Newman et al.

(10) Patent No.: US 6,949,629 B2
(45) Date of Patent: Sep. 27, 2005

(54) METHODS FOR PURIFYING SELECTED CEA FAMILY MEMBER PROTEINS

(75) Inventors: Diane Newman, Littleton, CO (US); Cathy Landmann, Highlands Ranch, CO (US); Mark Colgin, Castle Rock, CO (US)

(73) Assignee: AspenBio, Inc., Castle Rock, CO (US)

( * ) Notice: Subject to any disclaimer, the term of this patent is extended or adjusted under 35 U.S.C. 154(b) by 31 days.

(21) Appl. No.: 10/097,447

(22) Filed: Mar. 13, 2002

(65) Prior Publication Data

US 2003/0176646 A1 Sep. 18, 2003

(51) Int. Cl.[7] .............................. C07K 1/14; C07K 1/18; C07K 1/34
(52) U.S. Cl. .......................... 530/412; 530/414; 530/416
(58) Field of Search ................................. 514/2, 21, 25, 514/23, 42; 530/412, 414, 416, 300, 322, 324–330, 350, 380, 395, 422

(56) References Cited

U.S. PATENT DOCUMENTS

| | | |
|---|---|---|
| 3,867,363 A | 2/1975 | Hansen .................... 260/112 R |
| 3,956,258 A | 5/1976 | Hansen .................... 260/112 R |
| 4,086,217 A | 4/1978 | Hansen .................... 260/112 R |
| 4,140,753 A | 2/1979 | Edgington et al. ............. 424/1 |
| 4,145,336 A | 3/1979 | Edgington et al. ....... 260/112 R |
| 4,180,499 A | 12/1979 | Hansen .................... 260/112 R |
| 4,180,556 A | 12/1979 | Kim et al. ..................... 424/1 |
| 4,228,236 A | 10/1980 | Jakstys et al. .................. 435/1 |
| 4,272,504 A | 6/1981 | Kim et al. ..................... 424/1 |
| 4,299,815 A | 11/1981 | Hansen et al. .................. 424/1 |
| 4,349,528 A | 9/1982 | Koprowski et al. ............. 424/1 |
| 4,471,057 A | 9/1984 | Koprowski et al. ......... 436/518 |
| 4,818,709 A | 4/1989 | Primus et al. ............... 436/518 |
| 4,863,853 A | 9/1989 | Bartos et al. ................... 435/7 |
| 4,871,834 A | 10/1989 | Matsuoka et al. .......... 530/387 |
| 5,122,599 A | 6/1992 | Barnett et al. ................. 536/27 |
| 5,200,316 A | 4/1993 | Elting et al. .................... 435/6 |
| 5,231,009 A | 7/1993 | Barnett et al. ............ 435/240.2 |
| 5,274,087 A | 12/1993 | Barnett et al. .............. 536/23.5 |
| 5,545,532 A | 8/1996 | Codington et al. ......... 435/7.23 |
| 5,571,710 A | 11/1996 | Barnett et al. ............. 435/240.1 |
| 5,672,513 A | 9/1997 | Terskikh et al. ............... 436/64 |
| 5,693,763 A | 12/1997 | Codington et al. ....... 530/387.7 |
| 5,698,530 A | 12/1997 | Schlom et al. ................. 514/44 |
| 5,808,005 A | 9/1998 | Codington et al. .......... 530/395 |
| 5,837,824 A | 11/1998 | Bosslet et al. ............... 530/395 |
| 5,843,761 A | 12/1998 | Barnett et al. ......... 435/252.33 |
| 6,013,772 A | 1/2000 | Barnett et al. .......... 530/387.71 |
| 6,022,958 A | 2/2000 | Barnett et al. .............. 536/23.1 |
| 6,242,204 B1 | 6/2001 | Torczynski et al. ........ 435/7.23 |

FOREIGN PATENT DOCUMENTS

| | | | | |
|---|---|---|---|---|
| EP | 0 102 008 | 8/1983 | .......... | A61K/39/00 |
| EP | 0 212 880 | 7/1986 | ........... | C12P/21/00 |
| EP | 0 343 946 | 5/1989 | ............ | C07K/7/10 |
| EP | 0 346 710 A2 | 6/1989 | ........... | C12N/15/00 |
| EP | 0 346 710 B1 | 6/1989 | ........... | C12N/15/12 |
| EP | 1 090 927 | 10/1999 | ........... | C07K/16/00 |
| WO | WO 84/02983 | 8/1984 | .......... | G01N/33/54 |
| WO | WO 95/32286 | 11/1995 | ........... | C12N/15/12 |
| WO | WO 99/19478 | 4/1999 | ........... | C12N/15/12 |
| WO | WO 01/24832 | 4/2001 | .......... | A61K/48/00 |
| WO | WO 01/27159 | 4/2001 | .......... | C07K/16/00 |
| WO | WO 01/55337 | 8/2001 | | |

OTHER PUBLICATIONS

Calbiochem 1996–1997 Catalog, 1996, p. 76.*
abstract of Hammarstrom (Tumour Biology, 2000, vol. 21, Suppl. 1, p. 42).*
Sandy et al (Journal of Biological Chemistry, 1990, vol. 265, pp. 21108–21113).*
Pharmacia, Ion Exchange Chromatography, 1991, pp. 7–9.*
Aitio, M–L et al., "The electrophoretic heterogeneity of carcinoembryonic antigen," (1978) *Febs Letters* 93(1):29–32.
Arlen, P. et al., "The use of a rapid ELISPOT assay to analyze peptide–specific immune responses in carcinoma patients to peptide vs. recombinant poxvirus vaccines," (Jul. 2000) *Cancer Immunol. Immunother.* 49:517–529.
Ashman, L.K. and de Young, N.J., "Immunoadsorbent purification of the carcinoembryonic antigen," (1977) *Immunochemistry* 14:329–336.
Banjo, C. et al., "Preparation and isolation of immunologically active glycopeptides from carcinoembryonic antigen (CEA)," (1974) *Int. J. Cancer* 13:151–163.
Banjo C. et al., "Intermolecular heterogeneity of the carcinoembryonic antigen," (1974) *Cancer Res.* 34:2114–2121.
Boenisch, T. and Norgaard–Pedersen, B., "Carcinoembryonic antigen (CEA) of human tissue extracts: partial characterization of two variants separated by affinity chromatography on concanavalin A," (1975) *Clinica Chimica Acta* 60:51–57.
Carrico, R.J. and Usategui–Gomez, M., "The isolation of carcinoembryonic antigen from tumor tissue at neutral pH," (1975) *Cancer Res.* 35:2928–2934.

(Continued)

*Primary Examiner*—Karen A. Canella
(74) *Attorney, Agent, or Firm*—Greenlee, Winner and Sullivan

(57) ABSTRACT

Improved methods are provided for purifying selected carcinoembryonic antigen (CEA) family member proteins. Disclosed method steps include cation-exchange chromatography below pH 4.0 and size-exclusion chromatography, and do not include use of perchloric acid or antibody affinity steps. The resulting purified proteins are of at least 90% purity, substantially free of cross-reacting antigens, substantially free of CA19-9, substantially free of endotoxins, and substantially free of antibodies. Purities of greater than 98% have been achieved. Purified CEA family member proteins used as reference standards, in pharmaceutical carriers, and formulated as vaccines are disclosed. The purification, compositions, and use of CEA family member proteins containing altered immunogenic epitopes are also disclosed.

24 Claims, 3 Drawing Sheets

OTHER PUBLICATIONS

Cho, B.K. et al., "A yeast surface display system for the discovery of ligands that trigger cell activation," (1998) *J. Immunol. Meth.* 220:179–188.

Chu, T.M. et al., "The reaction between carcinoembryonic antigen and concanavalin A," (1974) *Cancer Res.* 34:212–214.

Colcher, D. et al., "Differential binding to human mammary and nonmammary tumors of monoclonal antibodies reactive with carcinoembryonic antigen," (1983) *Cancer Investigation* 1(2):127–138.

Coligan, J.E. et al., "Heterogeneity of the carcinoembryonic antigen," (1973) *Immunochemistry* 10:591–599.

Coligan, J.E. et al., "Isolation and characterization of carcinoembryonic antigen," (1972) *Immunochemistry* 9:377–386.

Coligan, J.E. and Slayter, H.S., "Physical, chemical and immunological characterization of saline–extracted, concanavalin A–purified carcinoembryonic antigen," (1979) *Molecular Immunology* 16:129–135.

Conry, R.M. et al., "Human immune response to carcinoembryonic antigen tumor vaccines," (1995) *J. Immunother.* 18(2):137, abstract.

Cutler, P., "Size–exclusion chromatography" (1996) *Methods in Molecular Biology,* S. Doonan, Ed., Humana Press, Totowa, NJ, 255–267.

Duffy, M.J., "Clinical uses of tumor markers: a critical review," (2001) *Critical Reviews in Clin. Lab. Sci.* 38(3):255–262.

Duraiswami, S. et al., "An evaluation of some methods for the isolation of carcinoembryonic antigen," (1976) *Cancer Related Antigens,* P. Franchimont Ed., North–Holland Publishing Co., Amsterdam–New York–Oxford, pp 23–35.

Duraiswami, S. et al., "An improved method for the isolation of carcinoembryonic antigen," (1976) *IRCS Medical Science* 4:172.

Dykes, P.W. and King, J., "Progress report carcinoembryonic antigen (CEA)," (1972) *Gut* 13:1000–1013.

Egan, M.L. et al., "Physical characterization and structural studies of the carcinoembryonic antigen," (1976) *Cancer Res.* 35:3482–3485.

Egan, M.L. et al., "Isolation and immunochemical and chemical characterization of carcinoembryonic antigen–like substances in colon lavages of healthy individuals," (1977) *Cancer Res.* 37:2638–2643.

Eveleigh, J.W., "Heterogeneity of carcinoembryonic antigen," (1974) *Cancer Res.* 34:2122–2124.

Foon, K.A. et al., "Immune response to the carcinoembryonic antigen in patients treated with an anti–idiotype antibody vaccine," (1995) *J. Clin. Invest.* 96:334–342.

Ford, C.H.J. et al., "Immunoadsorbent purification of carcinoembryonic antigen using a monoclonal antibody: a direct comparison with a conventional method," (1987) *Tumor Biol.* 8:241–250.

Frängsmyr, L. et al., "Four carcinoembryonic antigen subfamily members, CEA, NCA, BGP and CGM2, selectively expressed in the normal human colonic epithelium, are integral components of the fuzzy coat," (1999) *Tumor Biol.* 20:277–292.

Fritsche, R. and Mach, J–P, "Isolation and characterization of carcinoembryonic antigen (CEA) extracted from normal human colon mucosa," (1977) *Immunochemistry* 14:119–127.

Fritz, J.S. and Gjerde, D.T., "Ion Chromatography" (2000) Wiley–VCH Berlang GmbH, Weinheim, Germany, pp. 1–9, 23–27, 50–55, 81–93, 141–164, and 190–191.

Gold, P. and Freedman, S.O., "Specific carcinoembryonic antigens of the human digestive system," (1965) *J. Exp. Med.,* 122:467–481.

Gold, P. and Goldenberg, N.A., "The carcinoembryonic antigen (CEA): past, present and future," (1997) *McGill Journal of Medicine,* 3:46–66.

Grunert, F. et al., "Isolation and characterization of two proteins copurifying with carcinoembryonic antigen," (1984) *Tumour Biol.* 5:221–232.

Hammarström, S., "The carcinoembryonic antigen (CEA) family: structures, suggested functions and expression in normal and malignant tissues," (1999) *Cancer Biol.* 9:67–81.

Hammarström, S. and Baranov, V., "Is there a role for CEA in innate immunity in the colon?" (Mar. 2001) *Trends in Microbiology* 9:119–125.

Hammarström, S. "The nature and expression of the human CEA family," (1997) *Cell Adhesion and Communication Mediated by the CEA Family: Basic and Clinical Perspectives,* Stanners, C. Ed., Harwood Acad. Publishers, Amsterdam, pp 1–30.

Harvey, S.R. and Chu, T.M., "Demonstration of two molecular variants of carcinoembryonic antigen by concanavalin A sepharose affinity chromatography," (1975) *Cancer Res.* 34:3001–3008.

Hedin, A. et al., "Epitope specificity and cross–reactivity pattern of a large series of monoclonal antibodies to carcinoembryonic antigen," (1986) *Molecular Immunology* 23(10):1053–1061.

Hefta, L.J.F. et al., "Expression of carcinoembryonic antigen and its predicted immunoglobulin–like domains in HeLa cells for epitope analysis," (1992) *Cancer Res.* 52:5647–5655.

Hefta, S.A. et al., "Carcinoembryonic antigen is anchored to membranes by covalent attachment to a glycosylphosphatidylinositol moiety: identification of the ethanolamine linkage site," (1988) *Proc. Natl. Acad. Sci. USA* 85:4648–4652.

Herrmann, A. et al., "Studies on the 'insoluble' glycoprotein complex from human colon," (May 1999) *J. Biol. Chem.* 274(22):15828–15836.

Hill, R. et al., "Isolation of tumour–associated immunoglobulins from ascitric fluid," (1978) *Br. J. Cancer* 38:154–157.

Hill, R. et al., "A comparison of the physicochemical properties of carcinoembryonic antigen in extracts of tumour tissue, ascitic and cyst fluid from ovarian cancer," (1981) *AJEBAK* 59(4):469–476.

Hill, R. et al., "Nature of carcinoembryonic antigen purified from malignant ascitic fluid of serous cystadenocarcinoma of the ovary," (1981) *Molecular Immunology* 18(7):647–653.

Hörig, H. et al., "Strategies for cancer therapy using carcinoembryonic antigen vaccines," (Apr. 19, 2000) *Expert Reviews in Molecular Med.,* pp. 1–24.

Huber, M. et al., "The carboxyl–terminal region of biliary glycoprotein controls its tyrosine phosphorylation and association with protein–tyrosine phosphatases SHP–1 and SHP–2 in epithelial cells," (1999) *J. Biol. Chem.* 274(1):335–344.

Kantor, J. et al., "Antitumor activity and immune responses induced by a recombinant carcinoembryonic antigen–vaccinia virus vaccine," (1992) *J. Natl. Cancer Inst.* 84:1084–1091.

Kass, E. et al., "Induction of protective host immunity to carcinoembryonic antigen (CEA), a self–antigen in CEA transgenic mice, by immunizing with a recombinant vaccinia–CEA virus," (1999) *Cancer Res.* 59:676–683.

Kaufman, H. et al., "A recombinant vaccinia virus expressing human carcinoembryonic antigen (CEA)," *Int. J. Cancer* 48:900–907.

Keep, P.A. et al., "Extraction of CEA from tumour tissue, foetal colon and patients' sera, and the effect of perchloric acid," (1978) *Br. J. Cancer* 37:171–181.

Keep, P.A. and Rogers, G.T., "Heat–labile CEA," (1979) *Pro. Biol. Fluid Proc. Colloq.* 27:41–44.

Kersh, G.J. and Allen, P.M., "Structural basis for T cell recognition of altered peptide ligands: a single T cell receptor can productively recognize a large continuum of related ligands," (1996) *J. Exp. Med.* 184:1259–1268.

Kimball, P.M. and Brattain, M.G., "A comparison of methods for the isolation of carcinoembryonic antigen," (1978) *Cancer Res.* 38:619–623.

Koprowski, H. et al., "Colorectal carcinoma antigens detected by hybridoma antibodies," (1979) *Somatic Cell Genetics* 5(6):957–972.

Krupey, J. et al., "The preparation of purified carcinoembryonic antigen of the human digestive system from large quantities of tumor tissue," (1972) *Immunochemistry* 9:617–622.

Krupey, J. et al., "Purification and characterization of carcinoembryonic antigens of the human digestive system," (1967) *Nature* 215:67–68.

Kuroki, M. et al., "Purification and characterization of carcinoembryonic antigen–related antigens in normal adult feces" (1981) *Cancer Res.* 41:713–720.

Kuroki, M. et al., "Antigenic reactivities of purified preparations of carcinoembryonic antigen (CEA) and related normal antigens using four different radioimmunoassay systems for CEA," (1982) *J. Immunological Methods* 60:221–233.

Laurence, D.J.R. et al., "First British standard for carcinoembryonic antigen," (1975) *Br. J. Cancer* 32:292–299.

Matsuoka, Y., "Cancer specificity problems of carcinoembryonic antigen," (1976) *Cancer Related Antigens: Proceedings of th Euro. Econ. Comm. Symposium held at Liege, May 3–4, 1976,* Amsterdam: North–Holland Pub. Co.

Matsuoka, Y. et al., "Preparation and evaluation of antisera directed against cancer specific moiety of antigenic determinants on carcinoembryonic antigen," (1975) *Immunochemistry* 12:779–782.

Matsuoka, Y. et al., "Proteolytic release of antigenic fragments corresponding to normal fecal antigen and non–specific cross–reacting antigen from carcinoembryonic antigen," (1978) *Int. J. Cancer* 21:604–610.

Matsuoka, Y. et al., "Highly effective extraction of carcinoembryonic antigen with phosphatidylinositol–specific phospholipase C," (1991) *Tumor Biol.* 12:91–98.

Meltzer, M.S. et al, "Tumor–specific antigen solubilized by hypertonic potassium chloride," (1971) *J. Nat. Cancer Inst.* 47:703–709.

Mistretta, A.P. et al., "Isolation of a carcinoembryonic antigen (CEA) from a liver metastasis of primary adenocarcinoma of the colon and preparation of the specific antiserum," (1974) *Specialia, Experientia* 39(10):1209–1210.

Newman, E.S., "Interrelationship of carcinoembryonic antigen and colon carcinoma antigen–III," (1974) *Cancer Res.* 34:2125–2130.

Obayashi, Y. et al., "Role of carbohydrate antigens sialyl lewis (a) (CA 19–9) in bronchoalveolar lavage in patients with pulmonary fibrosis," (2000) *Respiration* 67:148–152.

Oikawa, Shinzo et al., "Primary structure of human carcinoembryonic antigen (CEA) deducted from cDNA sequence," (1987) *Biochem. and Biophys. Res. Comm.* 142(2):511–518.

Park, J–G et al., "Characteristics of cell lines established from human colorectal carcinoma," (1987) *Cancer Res.* 47:6710–6718.

Plow, E.F. and Edgington, T.S., "Isolation and characterization of a homogeneous isomeric species of carcinoembryonic antigen: CEA–S," (1975) *Int. J. Cancer* 15:748–761.

Poretz, R.D. and Goldstein, I.J., "An examination of the topography of the saccharide binding sites of concanavalin A and of the forces involved in complexation," (1970) *Biochemistry* 9(14):2890–2896.

Price, M.P. et al., "Association of the Y hapten with glycoproteins, glycolipids and carcinoembryonic antigen in colorectal carcinoma," (1986) *Cancer Lett.* 33:83–89.

Pritchard, D.G. and Egan, M.L., "Isolation of carcinoembryonic antigen by an improved procedure," (1978) *Immunochemistry* 15:385–387.

Pusztaszeri, G. and Mach, J–P, "Carcinoembryonic antigen (CEA) in non digestive cancerous and normal tissues," (1973) *Immunochemistry* 10:197–204.

Ritschard, W.J. and LeDain, M., "A simple method for the purification of the carcinoembryonic antigen without the use of perchloric acid," (1983) *Experientia* 39:375–377.

Rogers, G.T., "Heterogeneity of carcinoembryonic antigen implications on its role as a tumour marker substance," (1976) *Biochimica et Biophysica Acta* 355–373.

Rogers, G.T., "Heterogeneity of carcinoembryonic antigen and its fractionation by con A affinity chromatography," (1974) *Nature* 519–521.

Rogers, G.T. et al., "Application of monoclonal antibodies to purified CEA in clinical radioimmunoassay of human serum," (1981) *Br. J. Cancer* 44:371–380.

Rogers, G.T. et al., "Carcinoembryonic antigen: isolation of a subfraction with high specific activity," (1976) *Br. J. Cancer* 33:357–362.

Rogers, G.T. et al., "Heterogeneity and specificity of circulating carcinoembryonic antigen," (1977) *Eur. J. Cancer* 13:293–295.

Rosai, J. et al., "Membrane antigens of human colonic carcinoma and non–tumoral colonic mucosa: results obtained with a new isolation method," (1972) *Int. J. Cancer* 10:357–367.

Rule, A.H. and Goleski–Reilly, C., "Carcinoembryonic antigen (CEA) 'Fingerprints'," (1973) *Br. J. Cancer* 28:464–468.

Rule, A.H. and Goleski–Reilly, C., "Phase–specific oncocolon antigens: a theoretical framework for 'carcinoembryonic antigen' specificities," (1974) *Cancer Res.* 34:2083–2087.

Santen, R.J. et al., "Partial purification of carcinoembryonic–reactive antigen from breast neoplasms using lectin and antibody affinity chromatography," (1980) *Cancer Res.* 40:1181–1188.

Schlom, J., "Carcinoembryonic antigen (CEA) peptides and vaccines for carcinoma," in *Peptide–Based Cancer Vaccines,* W. Martin Kast Ed., (2000).

Schrewe, H. et al., "Cloning of the compl4ete gene for carcinoembryonic antigen: analysis of its promoter indicates a region conveying cell type–specific expression," (1990) *Molecular and Cellular Biology* 10(6):2738–2748.

Sheehan, D. and FitzGerald, R., "Ion–exchange chromatography" (1996) *Methods in Molecular Biology,* S. Doonan, Ed., Humana Press, Totowa, NJ, 145–150.

Slayter, H.S. and Coligan, J.E., "Characterization of carcinoembryonic antigen fractionated by concanavalin A chromatography," (1976) *Cancer Res.* 36:1696–1704.

Thompson, J. and Zimmerman, W., "The carcinoembryonic antigen gene family: structure, expression and evolution," (1988) *Tumor Biol.* 9:63–83.

Tu, Y.Y. et al., "Purification and characterization of carcinoembryonic antigen from GW–39, a xenografted human colonic tumor system," (1988) *Tumor Biol.* 9:212–220.

Virji, M., "CEA and innate immunity," (Jun. 2001) *Trends in Microbiology* 9(6):258–59.

Watt, S.M. et al., "CD66 identifies a neutrophil–specific epitope within the hematopoietic system that is expressed by members of the carcinoembryonic antigen family of adhesion molecules," (1991) *Blood* 78(1):63–74.

You, Y.H. et al., "Expression, purification, and characterization of a tow domain carcinoembryonic antigen minigene (N–A3) in pichia pastoris. The essential role of the N–domain," (1998) *Anticancer Research* 18:3193–3202.

Zaremba, S. et al., "Identification of an enhancer agonist cytotoxic T lymphocyte peptide from human carcinoembryonic antigen," (1997) *Cancer Res.* 57:4570–4577.

Zawadzka, E. et al., "Differences in the purification effect of carcinoembryonic antigen from the three different hepatic metastases of rectum carcinoma," (1979) *Neoplasma* 26:157–167.

Zhou, G–Q et al., "The carcinoembryonic antigen (CEA) gene family in non–human primates," (Feb. 2001) *Gene* 264(1)–105–112.

Zhu, M. et al., "Generation of specific anti–human carcinoembryonic antigen (CEA) cytotoxic T lymphocytes from a colon carcinoma patient immunized with recombinant vaccinia–CEA (rV–CEA) vaccine by stimulation with a CEA synthetic peptide (CAP–2) in vitro," (1996) *J. Immunother.* 19:459 (abstract only).

Zimmerman, R. and Hammaström, S., "Isolation of CEA–like material from urinary bladder carcinoma," (1978) *Urol. Res.* 6(4):215–219.

Krop–Watorek, A. et al., "Adhesive properties of carcinoembryonic antigen glycoforms expressed in glycosylation––deficient Chinese hamster ovary cell lines," (2002) *Acta Biochimica Polonica* 49(1):273–283.

El–Sadek, S. et al., "Carcinoembryonic antigen (CEA) in cervical neoplasia," found at: http://www.obgyn.net/displayarticle.asp?page=/english/pubs/articles/cea–review.

* cited by examiner

SEQUENCE LISTING

```
<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Tyr Leu Ser Gly Ala Asn Leu Asn Leu
1               5

<210> SEQ ID NO 2
<211> LENGTH: 9
<212> TYPE: PRT
<213> ORGANISM: Homo sapiens

<400> SEQUENCE: 2

Tyr Leu Ser Gly Ala Asp Leu Asn Leu
1               5
```

METHODS FOR PURIFYING SELECTED CEA FAMILY MEMBER PROTEINS

BACKGROUND OF THE INVENTION

Carcinoembryonic antigen, CEA, was first described in 1965 as cancer-specific fetal antigen in adenocarcinoma of the human digestive tract. In 1986, the CEACAM5 gene (carcinoembryonic antigen cell adhesion molecule 5) that encodes human CEA was localized to chromosome 19, and in 1987 it was cloned.

CEA is a 180 kD glycoprotein that is anchored to the cell membrane by a glycosylphosphatidylinositol (GPI) lipid moiety. CEA is heavily glycosylated, approximately 60% by weight (Egan, M. L. et al. (1976) Cancer Research 36:3482–3485). CEA has only been found in humans. CEA has many family members, including many cross-reacting antigens, some of which have been found in other species. CEA protein is found at high levels in the fetal colon and lower levels in the normal adult colonic epithelium. Levels of CEA can become elevated when inflammation or tumors arise in any endodermal tissue, including in the gastrointestinal tract, respiratory tract, pancreas, and breast. CEA is present at abnormally high levels in several benign disorders and in malignant tumors, including those of the stomach, small intestine, colon, rectum, pancreas, liver, breast, ovary, cervix, and lung. Non-malignant disorders showing high levels of CEA include: diverticulitis, pancreatitis, inflammatory bowel disease, cirrhosis, hepatitis, bronchitis, and renal failure. CEA is also elevated in individuals who smoke.

The function of CEA in normal colon epithelial cells is still being investigated. It is thought that CEA, which is localized on the cell surface, acts as a homotypic adhesion molecule, resulting in aggregation of CEA-expressing cells. The pattern of localization is different in colon tumor cells compared to normal colon cells. In the normal colonocytes, CEA is localized only at the luminal surface of cells, whereas in tumor cells, it is found in a disoriented pattern throughout the cell membrane. The altered pattern in tumor cells may disrupt the intercellular adhesion resulting in the disorganized growth and movement of malignant cells. CEA and its closely related family members have also been shown to participate in signal transduction. In normal human colon, CEA is released from cells via pinching off of CEA-coated vesicles. More than 90% of total CEA in normal feces is membrane bound. It has also been theorized that CEA might play a role in innate immunity by binding and trapping microorganisms in the digestive tract and other tissues (Frangsmyr, L. et al. (1999) Tumor Biology 20:277–292 and Hammarstrom, S. and Baranov, V. (2001) Trends in Microbiology 9(3):119–125). This binding would prevent the microorganisms from reaching and invading epithelial cells of the microvilli. The constant and rapid release of CEA-containing vesicles could provide a method for constant trapping and rapid release of bacteria.

The CEA gene (Genbank Accession Number M17303) encodes an mRNA of 3100 nucleotides and translates into a 702 amino acid protein that is cleaved of a 34-amino-acid signal sequence to form a 668 amino acid protein of 70 kD (Oikawa, S. et al. (1987) Biochemical and Biophysical Research Communications 142:511–518). Upon attachment to the cell membrane via a GPI anchor, a 26-amino-acid C-terminal sequence, called the M-domain, is cleaved. This protein is heavily glycosylated, leading to a final weight of 180 kD. Amino acid sequence analyses have shown that CEA is a member of the immunoglobulin supergene family. CEA has an N-terminal N domain of 108 amino-acids that is similar to the immunoglobulin variable domain IgV, and then six domains, A1-B1-A2-B2-A3-B3, that are similar to the immunoglobulin constant domain IgC. Each A-B pair comprises 178 amino acids. Each domain of CEA is encoded by a separate exon. All known CEA family members that are translated have an N domain; they differ in the number and organization of IgC-like domains, the presence or absence and method of membrane attachment, and the presence or absence of a cytoplasmic domain. CEA does not have a cytoplasmic domain. Proteins of the CEA family are highly glycosylated.

The human CEA gene family currently consists of thirty genes (CEACAM1, CEACAM3–CEACAM8, AG128375, PSG1–PSG11, and CEACAM-ps1-CEACAM-ps11) and is divisible into three subgroups: thirteen CEA cross-reacting genes of which eight (CEACAM1, CEACAM3–CEACAM8 and AG128375) are expressed Frangsmyr, L. (1999) Tumor Biology 20:217–292, and Potera, C. (2001) Genetic Engineering News 21(12):9), eleven pregnancy-specific glycoproteins (PSG1–PSG11) of which at least nine expressed, and six unexpressed pseudogenes. PSG Accession Numbers include: M20882, M23575, M25384, U18467, U25988, M21822, M17908, M20879, J04539, M34715, M33665, U18469, M33666, M31125, X17610, U25987, and M31126. Only some CEA family members are present in primates, suggesting that the CEA family is undergoing strong selection and rapid evolution.

The CEA subfamily of cross-reacting antigens in humans, includes eight expressed genes including: CEACAM1 (CEACAM1-4L for biliary glycoprotein or BGP), CEACAM3 (CEACAM3-1L), CEACAM4 (CEACAM4), CEACAM5 (carcinoembryonic antigen or CEA), CEACAM6 (non-specific cross-reacting antigen or NCA), CEACAM7 (CEACAM7-2), CEACAM8 (CEACAM8) and AG128375. CEACAM1 (CEACAM1-4L) encodes thirteen splice variants (Genbank Accesion Numbers: D12502, X16354, X14831, S71326, X16356, D9031 1, D90312, D90313, E03350, E03351, E03352, M76742, M76743, D12502, and M76744) that contain zero to three IgC-like domains, membrane-spanning domains with cytoplasmic domains in some, with others not attached to the membrane, and two with additional extracellular Alu repeat sequences (CEACAM5 has Alu repeats that are untranslated). The CEACAM1 proteins range in size from about 80 kd to about 160 kd. CEACAM3 encodes three splice variants (Genbank Accession Numbers: L00692, D90277, D90278 and L00693) that contain no IgC-like domains; one variant is not attached to the membrane and two are attached with hydrophobic membrane-spanning domains and cytoplasmic domains. CEACAM7 encodes two splice variants (Genbank Accession Numbers X98311 and AF006623), one of which has one IgC-like domain (the other has none), with both attached via GPI anchors. CEACAM4-6 and -8 are not known to have splice variants. CEACAM4 (Genbank Accession Number D90276) encodes one IgC-like domain and is attached with a membrane spanning domain and a cytoplasmic domain. CEACAM5, CEA, is described above. CEACAM6 (NCA) encodes one AB pair of IgC-like domains and is attached via a GPI anchor. NCA (Genbank Accession Numbers M29541 and M18728) is present in two forms, 50 kD and 90 kD. CEACAM8 (CEACAM8) encodes an AB pair of IgC-like domains and is attached via a GPI anchor. The CEACAM8 protein is about 95 kD (Hammarstrom, S. et al. (1997) "The Nature and Expression of the Human CEA Family" in *Cell Adhesion and Commu-*

*nication Mediated by the CEA Family: Basic and Clinical Perspectives*, Stanners, C. Ed., pp 1–30, Harwood Acad. Publishers, Amsterdam).

CEA and CEACAM7 are expressed in epithelial cells, CEACAM3 and CEACAM8 in granulocytic cells, and CEACAM1 and CEACAM6 in many cell types, including epithelial cells. CEA is expressed in columnar epithelial cells and goblet cells of the colon, in mucous neck cells and pyloric mucous cells in the stomach, in squamous epithelial cells of the tongue, esophagus and cervix, in secretory epithelia and duct cells of sweat glands, and, in epithelial cells of the prostate (Hammarstrom, S. (1999) Seminars in Cancer Biology 9:67–81).

In situ hybridization, immunohistochemistry, and immunoelectron microscopy show CEACAM5 (CEA) and CEACAM6 (NCA) to have very similar expression patterns (Frangsmyr, L. (1999) Tumor Biology 20:277–292). An example of a tissue that expresses NCA and not CEA is squamous carcinoma of the lung. Mature NCA is 310 amino acids, after a 34 amino acid leader peptide is cleaved. BLAST analysis of CEA and NCA mature proteins demonstrates that NCA has about 86% amino acid identity with CEA (Thompson, J and Zimmermann, W. (1988) Tumor Biology 9:63–83).

In May 2001 a new cancer antigen, the eighth expressed member of the CEA cross-reacting subgroup, was cloned by AlphaGene. AG128375 was reported in the press as a splice variant of CEA Potera, C. (2001) Genetic Engineering News 21(12):9–10), but actually it is a completely new gene that is a member of the CEA gene family. It resides on a different chromosome from CEA and is prostate specific, Like CEA, AG128375 has an N domain and 6 IgC-like domains in the same order. AG128375 is expressed in normal and cancerous prostate tissue as well as in prostate tissue that has metastasized to the bone marrow, as shown by testing prostate-derived metastatic bone marrow cell lines. AG128375 is approximately the sane size as CEA and is likely to be similarly glycosylated, but it is expressed in a different distribution of tissues.

Although CEA has only been identified in humans, other members of the CEA gene family have been shown to exist in other species. CEA family members have been identified in mice, rats, guinea pigs, and non-human primates (http://www.med.uni-muenchen.de/cea/contents/introduction.htm).

Currently, colorectal cancer is the second most prevalent cancer in the United States and the presence or absence of CEA plays multiple roles in the fight against cancer. CEA is considered a tumor marker, but because it is expressed in so many normal and benign tissues, it is not a useful marker for cancer screening. However, CEA is a useful marker for predicting a patient's response to a therapy or tracking a patient's response throughout a therapy. In clinical medicine, CEA serum levels can assist in detecting advanced colorectal cancer as well as other various cancers. CEA levels generally increase with well-differentiated tumors and little increase is noted in poorly-differentiated adenocarcinomas. CEA blood concentration is used for monitoring cancer treatment. Patients determined to have high CEA levels before surgery always return to normal range post-operatively. An increase in the CEA level after successful surgery has been shown to indicate reoccurrence of the tumor (Wirakapun, S. (2001) Diseases of the Colon and Rectum 44:231–235; Miles, W. F. A (1995) Br. J. of General Practice 45:287–288; and Chu, D. Z. J. (1991) Archives of Surgery 126:314–316).

Assay methods for CEA are reported in the following publications. U.S. Pat. No. 4,180,556 (issued Dec. 25, 1979) reports a pretreatment method for CEA. Pretreatment of CEA, before immunoassays, comprises adding perchloric acid (PCA) to the sample, adding buffered source of potassium ions to precipitate the potassium perchlorate, and centrifuging to remove precipitate, thereby eliminating the need for dialysis after PCA treatment. U.S. Pat. No. 4,272,504 (issued Jun. 9, 1981) reports an antibody adsorbed support assay for CEA. U.S. Pat. No. 4,299,815 (issued Nov. 10, 1981) reports an improved process for radioimmunoassay of CEA. U.S. Pat. No. 4,349,528 (issued Sep. 14, 1982) reports an antibody specific for the 180 kd CEA. U.S. Pat. No. 4,818,709 (issued Apr. 4, 1989) reports an immunoassay for CEA and kits for such an assay. U.S. Pat. No. 4,863,853 (issued Sep. 5, 1989) reports a method of determining the value of monitoring CEA levels in patients undergoing therapy. U.S. Pat. No. 5,200,316 (issued Apr. 6, 1993) reports immunoassay methods using noncross-reactive CEA family antibodies. U.S. Pat. No. 6,013,772 (issued Jan. 11, 20000) reports CEA family antibodies and uses thereof. EPA 0343946 (published Nov. 29, 1989) reports synthetic CEA fragments that include a unique epitope, assays which utilize such fragments, and kits. Rogers, G. T. et al. (1981) Br. J. Cancer 44:371–380 describes a double antibody radioimmunoassay for CEA.

Members of the CEA gene family have been considered for use as vaccines, with hope that they might serve as antigenic targets for eliciting anti-cancer immune responses, for treatment and/or prevention. CEA family member proteins may play a role in cell aggregation, possibly as intercellular adhesion molecules, suggesting that vaccines targeting CEA family member proteins may be particularly useful for preventing metastasis. For CEA family member proteins to be used as vaccines, there must be sources of CEA family member proteins of sufficient purity and quantity. For this reason, as well as for basic research, there has been a long history of attempts to purify CEA family member proteins.

The first attempts to purify CEA family member proteins utilized a glycoprotein solvent extraction step followed by one or several forms of size-exclusion chromatography. The solvent of choice was initially PCA. Krupey, J. et al. (1967) Nature 215:67–68 describes the purification of CEA from the digestive system. CEA was purified by PCA extraction, paper block electrophoresis, and size-exclusion chromatography with Sephadex G-200. Coligan, J. E. (1972) Immunochemistry 9:377–386 describes isolation and characterization of CEA. CEA was isolated by PCA extraction, filtration, and size-exclusion chromatography using Sepharose 4B and Sephadex G-200. Krupey, J. (1972) Immunochemistry 9:617–622 describes purifying CEA from tumor tissue. CEA was purified by PCA extraction, sequential size-exclusion filters, gel-filtration chromatography, and size-exclusion chromatography using Sepharose 4B, Sephadex G-25, and Sephadex G-200. Banjo, C. et al. (1974) Cancer Research 34:2114–2121 describes the intermolecular heterogeneity of CEA. Purification of CEA was performed by the method of Krupey (1972). Laurence, D. J. R. et al., (1975) Br. J. Cancer 32:295–299 describes the first British Standard for CEA, prepared by PCA extraction and size-exclusion chromatography by Sepharose 4B and then Sephadex G-200. Matsuoka, Y. et al, (1975) Immunochemistry 12:779–782 describes attempts to identify anti-CEA antisera that was specific to the tumor-expressed form of CEA. CEA was partially purified by PCA extraction, ethanol precipitation, size filtration by successively smaller filters, and size-exclusion chromatography with Sepharose 4B. Kuroki, M (1981) Cancer Research 41:713–720 describes the purification and characterization of CEA from human feces. Purification of CEA was performed by the method of Krupey (1967) with additional gel filtration. Matsuoka, Y. (1976) "Cancer Specificity Problems of Carcinoembryonic Antigen" from Proceedings of the Euro. Econ. Comm. Symposium, pp 3–14 describes a CEA from human feces. CEA was prepared by PCA extraction, ethanol fractionation, and size-exclusion chromatography with Sepharose 4B. U.S. Pat. No. 4,871,834 (issued Oct. 3, 1989) reports monoclonal antibodies specific to CEA, the processes of making such antibodies, and the use of such antibodies. The antigenic CEA was prepared by PCA extraction followed by three steps of size-exclusion chromatography using Sepharose 4B, Sepharose 6B, and Sephadex G200. U.S. Pat. No. 4,228,236 (issued Oct. 14, 1980) reports CEA recombinant cell lines and recovering CEA from such cell lines utilizing PCA extraction.

There was controversy as to the effect of PCA, a strong acid, on the carbohydrate moieties on CEA family member proteins. Several groups attempted to use other methods to separate CEA family member proteins from cellular materials by shortening the PCA step or eliminating it altogether. Several different glycoprotein extraction or precipitation chemicals were utilized. Kimball, P. M. and Brattain, M. G. (1978) Cancer Research 38:619–623 describes a comparison of CEA purification methods. CEA was isolated by 1) saline-isolation, 2) saline-isolation and PCA extraction, or 3) saline-isolation and dialysis at pH 5 and heat treatment. Additional isolation procedures followed. Approximately 90% of the CEA antigenic activity was lost from each peak (identified with isoelectric focusing) after treatment with PCA. Carrico, R. J. et al. (1975) Cancer Research 35:2928–2934 describes a change in antigenicity of CEA with PCA extraction. CEA was isolated by Tris-acetate extraction at pH 6.9, anion-exchange chromatography, affinity chromatography with Con A, and size-exclusion chromatography with Sepharose 4B and Sephadex G200. Ritschard, W. J. (1983) Experientia 39:375–377 describes CEA purification without PCA. CEA was separated from other cellular components by polycarbonic acid extraction, followed by other techniques. Tu, Y. Y. et al. (1988) Tumor Biology 9:212–220 describes the purification of CEA from GW-39, a xenografted human colonic tumor system in hamsters. CEA was purified away from other cellular materials by acetic acid extraction followed by additional techniques. Duraiswami, S. et al. (1976) Intl Research Comm. Med. Science 4:172 extracted CEA with an 0.05M acetic acid-sodium acetate buffer at pH 4.5 also containing 40% ethanol, followed by acetone precipitation, ammonium sulfate extraction and precipitation, and size-exclusion chromatography at pH 4.0. Matsuoka, Y. et al, (1975) Immunochemistry 12:779–782 describes attempts to identify anti-CEA antisera that was specific to the tumor-expressed form of CEA. CEA was prepared by PCA extraction, ethanol precipitation, and other procedures. Rule, A. H. and Goleski-Reilly, C. (1973) Br. J. Cancer 28:464–468 and Rule, A. H. and Goleski-Reilly, C. (1974) Cancer Research 34:2083–2087 describe CEA fingerprints of various tissues. CEA was prepared by saline extraction, urea glycoprotein dissociation, and sucrose gradient electrofocusing chromatography. Radio-immunoassay (RIA) showed a change in CEA fingerprints with the use of PCA. Duraiswami, S. et al. (1976) "An evaluation of some methods for the isolation of CEA" in P. Franchimont Ed. Cancer Related Antigens pp 23–35, North Holland Publishing Co. and Duraiswami, S. et al. (1976) IRCS Med Sci: Immunol 4:172 describes an improved procedure for isolating CEA comprising: ethanol-acetate extraction, solubilizing the acetone powder with two extractions of distilled water, $(NH_4)_2SO_4$ fractionation, and two cycles of size-exclusion chromatography with Sephadex G200 at pH 4.0. Extracting with PCA resulted in a 75% loss of CEA antigenic activity. Rosai J. et al. (1972) Int. J. Cancer 10:357–367 describes CEA purification by extraction with 0.25M sucrose and TE (0.05M:0.002M), precipitation with 0.1M LiCl, extraction with 0.3M lithium diiodosalicylate at pH 7.5, extraction with 25% phenol, and precipitation with ethyl alcohol. Meltzer, M. S. et al. (1971) J. Nat. Cancer Inst. 47:703–709 describes the isolation of tumor-specific antigens by extraction in 3M hypertonic KCl, extraction with 0.1M NaCl, precipitation with 2M ammonium sulfate, and size-exclusion chromatography with Sephadex G200.

Lectin affinity-chromatography was also utilized, to further prepared CEA family member proteins (Chu, T. M. et al (1974) Cancer Research 34:212–214) or to avoid harsh chemical such as PCA. This approach was limited because many of the proteins isolated with CEA are also glycoproteins. Rogers, G. T. (1974) Nature 251:519–521 describes CEA isolated by Con A chromatography. CEA was isolated by the methods of Krupey (1972) and then by affinity chromatography using Con A Sepharose. Boenisch, T. and Nørgaard-Pedersen, B. (1975) Clinica Chimica Acta 60:51–57 describes two CEA variants, one reactive with Con A and the other not reactive with Con A, separated by Con A affinity chromatography. CEA was extracted by PCA extraction, size-exclusion chromatography with Sephadex G-200, affinity chromatography with Con A Sepharose, followed by an optional repeat of size-exclusion chromatography with Sephadex G-200. Rogers, G. T. et al. (1976) Br. J. Cancer 33:357–362 describes isolation of CEA. CEA was purified by Coligan, J. E. (1972) Immunochemistry 9:377–386 and affinity chromatography with Con A Sepharose, twice. Slayter, H. S. and Coligan, J. E. (1976) Cancer Research 36:1696–1704 describes CEA fractionated with Con A chromatography. CEA was fractionated by PCA extraction, size-exclusion chromatography with Sepharose 4B and Sephadex G-200, and affinity chromatography with Con A Sepharose. Egan, M. L. et al. (1977) Cancer Research 37:2638–2643 describes isolation of CEA-like substances from healthy colon tissue. CEA-like material was isolation by PCA extraction, size-exclusion chromatography with Sepharose 6B and Sephadex G-200, and affinity chromatography with Con A. Pritchard, D. G. and Egan, M. L. (1978) Immunochemistry 15:385–387 describes an improved procedure for isolating CEA. CEA was isolated by PCA extraction, ethanol precipitation, size-exclusion chromatography with Sepharose 4B, and affinity chromatography with Con A-Sepharose. Matsuoka, Y. et al. (1978) Int. J. Cancer 21:604–610 describes proteolytic release of antigenic fragments from CEA corresponding to cross-reacting antigens. CEA was prepared by PCA extraction, decreasing size membrane filtrations, size-exclusion chromatography with Sepharose 4B, 6B and Sephadex G-200. Another batch was prepared further by affinity chromatography with Con A Sepharose 4B. Coligan, J. E. and Slayter, H. S. (1979) Molecular Immunology 16:129–135 describes characterization of Con A purified CEA. A new method for purifying CEA was attempted because other references suggested that PCA purification was too harsh and alters the physical, chemical, and immunological properties of CEA. The tumor tissue used to purify CEA was homogenated in a PBS solution, dialyzed and lyophilized. CEA was purified from this material by Sepharose 4B chromatography twice, Sephadex G-200 chromatography, and then Con A Sepharose chromatography. Hill, R. (1981) Ajebak 59:469–476 describes CEA characteristics when extracted from different sources. CEA was prepared by PCA extraction, size-exclusion chromatography with Sephadex G-200, affinity chromatography with Con A, affinity chromatography with wheat germ lectin Sepharose 6 MB, and isoelectric focusing. CEA peaks were identified at pI3.2 and pI 4.4. Watt, S. M. et al. (1991) Blood 78:63–74 describes a neutrophil-specific epitope expressed by members of the CEA family. CEA was prepared by PCA extraction, size-exclusion chromatography with Sepharose 6B, and affinity chromatography with Con A sepharose. Harvey, S. R. and Chu, T. M. (1975) Cancer Research 35: 3001–3007 describes two molecular variants of CEA. CEA was separated by PCA extraction, affinity chromatography with Con A Sepharose, and size exclusion chromatography with Sephadex G-200. Keep, P. A. et al. (1978) Br. J. Cancer 37:171–182 describes the extraction of CEA and the effect of PCA. CEA was extracted by several versions of a PCA extraction, size-exclusion chromatography with Sepharose 6B and Sephadex G-200, and affinity chromatography with Con A Sepharose.

Immnuno-affinity chromatography using anti-CEA antibodies was used to even further purify CEA family member proteins. This approach was similarly limited as lectin affinity chromatography, because many proteins co-purifying with CEA share immunologic epitopes. Eveleigh J. W. (1974) Cancer Research 34:2122–2124 describes an isolation method that separates CEA from several proteins that had previously been isolated with CEA. These proteins were isolated by saline extraction, immuno-affinity chromatography, and anion-exchange chromatography at a range of salt concentrations, twice. At least eight peaks were observed. Previously generated "CEA" antibodies were made against all of these proteins. Acidic extraction with HCl at pH 3.0 yielded more of the basic components. PCA extraction yielded more of the acidic components. It was noted that size-exclusion chromatography would be ineffective at separating these components, as they are of similar molecular weights. Ashman, L. and De Young, N. J. (1977) Immunochemistry 14: 329–336 describes immunoadsorbent purification of CEA. Standard CEA was purified by PCA extraction, followed by size-exclusion chromatography with Sepharose 4B and Sephadex G200. Experimental CEA was purified by phosphate extraction, cotton filtration, and either immunoadsorbent precipitation with rabbit or goat anti-CEA antiserum (pH 6.5), or affinity chromatography with Con A. EPA 0102008 (published Mar. 7, 1984) reports CEA isolation, comprising PCA extraction, size filtration, anti-CEA affinity chromatography, and liquid chromatography. Price, M. R. et al. (1986) Cancer Letters 33:83–89 describes the association of the Y Hapten with CEA. Antigens were isolated with detergent and immuno-affinity chromatography. EPA 0212880 (published Mar. 4, 1987) reports production of CEA antigen comprising cultivating a CEA-producing cell line in monolayer culture with further cultivation steps, harvesting the medium containing the secreted CEA, and purification of CEA until iodination grade product was obtained. The purification steps comprised PCA and ammonium sulfate extractions, and immuno-affinity chromatography. CEA as a composition of matter having certain physical properties and immunoreactivity was reported. Tu, Y. Y. et al. (1988) Tumor Biology 9:212–220 describes the purification of CEA from GW-39, a xenografted human colonic tumor system in hamsters. CEA was purified by acetic acid extraction, affinity chromatography with anti-CEA, and size-exclusion chromatography with Sepharose Cl-6B. The purified CEA pI was 4.4. U.S. Pat. No. 5,672,513 (issued Sep. 30, 1997) reports CEA lacking the carboxyl terminal 26 amino acids and uses thereof. rCEA was purified by immuno-affinity chromatography, PCA extraction, and size-exclusion chromatography using Sephadex G-200 and Sepharose 6B. You, Y. H. et al. (1998) AntiCancer Research 18:3193–3202 describes the expression, purification, and characterization of a CEA minigene. Proteins were purified by PCA extraction and immuno-affinity chromatography.

Both types of affinity chromatography have been combined. Zimmerman, R. and Hammarström, S. (1978) Urological Res. 6:215–219 describes the isolation of CEA from bladder carcinoma. CEA was isolated by PCA extraction, size-exclusion chromatography with Sepharose 4B, and affinity chromatography with Con A and sheep anti-CEA serum. Santen, R. J. et al. (1980) Cancer Research 40:1181–1188 describes the partial purification of CEA from breast neoplasms. CEA was partially purified by 1) glass wool filtration, polyvalent immuno-affinity chromatography, wheat germ agglutinin lectin (alternative to Con A), Sepharose 4B affinity chromatography, hydroxylapatite precipitation, and ACA 34 gel filtration chromatography; 2) phenylmethyl sulfonyl fluoride/aminocaproic acid/EDTA/sodium azide proteolysis prevention step, monospecific immuno-affinity chromatography, and ACA 44 (34) chromatography; or 3) procedure 1) with the addition of a first proteolysis prevention step and also without lyophilization or freezing. Ritschard, W. J. (1983) Experientia 39:375–377 describes CEA purification without PCA. CEA was purified by polycarbonic acid extraction (not perchloric acid), size-exclusion chromatography with Sephadex G-200, and optionally affinity chromatography and/or immunoadsorption.

Anion-exchange chromatography has been an important tool for purifying CEA family member proteins. Anion exchange has been most common. Mistretta, A. P. et al. (1974) Experientia 30:1209–1210 describes CEA isolation from colon cancer tissue and generation of antiserum. CEA was isolated by PCA extraction, anion-exchange chromatography with DEAE-cellulose at pH 6.75, and size-exclusion chromatography with Sephadex G-200. Plow, E. F. and Edgington, T. S. (1975) Int. J. Cancer 15:748–761 describes the characterization of a CEA isomer, CEA-S. CEA-S was isolated by PCA extraction, isoelectric focusing, anion-exchange chromatography using DEAE cellulose, size-exclusion chromatography with Sephadex G-200, and immuno-affinity chromatography with anti-CEA (to remove CEA). Isopyknic density gradient ultracentrifugation was used to characterize the protein. CEA was isolated by PCA extraction and size-exclusion chromatography with agarose. Carrico, R. J. and Usategui-Gomez, M (1975) Cancer Research 35:2928–2934 describes the isolation of CEA from tumor tissue at neutral pH. CEA was isolated by anion exchange chromatography with DEAE-cellulose at pH 6.9, affinity chromatography with Con A Sepharose, size exclusion chromatography with Sepharose 4B and Sephadex G-200. Alternatively CEA was isolated by PCA extraction. Sixty to seventy percent of the CEA in crude tumor extracts or neutral pH isolations was destroyed and/or becomes insoluble under acidic conditions. Fritsche, R. and Mach, J. (1977) Immunochemistry 14:119–127 describes CEA from normal colon mucosa. CEA was isolated by 1) PCA extraction, size-exclusion chromatography with Sephadex G-200 and Sepharose 6B, and anion-exchange chromatography with DEAE at pH 7.4; or 2) by steps 1–2 above with the Sepharose 6B and anion-exchange chromatography optional; or 3) by steps 1–2 above followed by immuno-affinity precipitation with goat anti-CEA and another PCA extraction; or 4) by steps 1–2 above followed by immuno-affinity chromatography with goat anti-CEA. Lisowska, Z. et al. (1979) Neoplasma 26: 157–167 describes the purification of CEA from three different sources. CEA was purified by PCA extraction, size exclusion chromatography with Sepharose 4B and Sephadex G-200, affinity chromatography with Con A, and anion-exchange chromatography with DEAE. U.S. Pat. No. 4,145,336 (issued Mar. 20, 1979) reports the isolation and utilization of a CEA isomer. CEA-$S_1$ was isolated by PCA extraction, brought to pH 3–6, and iso-electric-focused. The peak at pI 4.4–4.6 was recovered, separated by size-exclusion chromatography (A-1.5 fine agarose and Sephadex G-200), further isolated by ion exchange chromatography (DEAE cellulose), and contaminants removed by immuuno-affinity chromatography. Isopyknic density gradient ultracentrifugation was also performed. U.S. Pat. No. 4,140,753 (issued Feb. 20, 1979) reports a radioimmunoassay for an isolated CEA isomer. CEA-$S_1$ was isolated by PCA extraction, brought to pH 3–6, and iso-electric-focused. The peak at pI 4.4–4.6 was recovered, separated by size-exclusion chromatography (Sephadex G-200), further isolated by ion exchange chromatography (DEAE cellulose at pH 8), and contaminants removed by immuno-affinity chromatography. Isopyknic density gradient ultracentrifugation was also performed. Kuroki, M. et at. (1982) J of Immunological Methods 60:221–233 describes antigenic reactivities of several preparations of purified CEA and related antigens. Antigens were extracted by the methods of Matsuoka, Y. et al, (1975) Immunochemistry 12:779–782) and Matsuoka, Y. et al. (1978) Int. J. Cancer 21:604–610. A combination of procedures including PCA extraction, affinity chromatography, size-exclusion chromatography (gel filtration, Sepharose 6B, Sephadex G-200, Sephadex G-100), and anion-exchange chromatography were used. Hedin, A. et al (1986) Molecular Immunology 23:1053–1061 describes monoclonal antibodies to CEA. CEA was purified by PCA extraction, anion exchange chromatography with DEAE Sephadex, size-exclusion chromatography with Sepharose 4B, affinity chromatography with Con A Sepharose, and size-exclusion chromatography with Sephadex G-200 or CEA was purified with immuno-affinity chromatography. Ford, C. H. J. et al. (1987) Tumor Biology 8:241–250 describes purifying CEA with monoclonal antibody immunoadsorbent precipitation. Conventional CEA was purified by PCA extraction, clarification with glass fiber filters, ethanol precipitation, phosphate resuspension, size-exclusion chromatography with Sepharose 4B and Sephacryl S300, anion-exchange chromatography with DEAE Sephacel at pH 8.3, and affinity chromatography with Con A Sepharose. Experimental CEA was purified by PBS extraction, buffer exchange with Sephadex G25, and immuno-affinity chromatography with 11-285-14 monoclonal anti-CEA antibody. Krupey, T. et al. (1974) Specialia 30:1209–1210 describe a method for purifying CEA comprising: PCA extraction, extraction in 3M KCl, 0.05M $NaH_2PO_4$ at pH 4.2, anion-exchange chromatography at pH 6.75, and size-exclusion chromatography at pH 4.5.

WO 95/32286 (published Nov. 30, 1995) reports recombinant CEA, lacking the transmembrane domain, expressed in insect cells using a baculovirus expression system, and methods of purifying such secreted CEA. Purification methods comprise chromatography utilizing four resins: hydrophobic interaction HIC ether 650 m, HIC Butyl 650M, lentil lectin Sepharose 4B, and DEAE (anion chromatography) Sepharose Fast Flow. Before chromatography, insect cell supernatant was acidified with acetic acid to pH 3.5 and incubated for one hour, in order to inactivate all viruses. The supernatant was then neutralized to pH 7.0 and filtered to remove precipitated viral and cellular proteins. rCEA was said to remain soluble throughout this step. The remainder of the purification process was carried out at neutral pH. The application also demonstrates the use of purified CEA (from Vitro Diagnostics) as a standard, for comparison of physical properties and for comparison of utility as a vaccine.

Mixed-bed ion-exchange chromatography using both anion- and cation-exchange resins has been used occasionally for the purification of CEA family member proteins. U.S. Pat. No. 3,867,363 (issued Feb. 18, 1975), U.S. Pat. No. 3,956,258 (issued May 1, 1976), U.S. Pat. No. 4,086,217 (issued Apr. 25, 1978), and U.S. Pat. No. 4,180,499 (issued Dec. 25, 1979) report methods for isolating, identifying, and detecting CEA material. CEA material was isolated by glycoprotein solvent extraction, gel-filtration, and mixed bed ion-exchange chromatography by eluting in ammonium acetate at pH 4. PCA extraction was preferred. Component A and component B, the isolated CEA material, range from 200–500 kD. Newman, E. S. et al. (1974) Cancer Research 34:2125–2130 describes isolation of CEA and CCA-III by PCA extraction, mixed-bed ion-exchange chromatography at pH 4.0, and size-exclusion chromatography with Sepharose 6B. Two forms of CEA, 180 kD and 200 kD were isolated together. CCA-III was reported to have contaminated the CEA preparation, by no more than 0.5%. CEA also was reported to have contaminated the CCA-III preparation, by less than 0.1%. WO 8402983 (published Aug. 2, 1984) reports CEA family antigens and antibodies and their methods of use. Antigens were purified by ethanol extraction, anion-exchange chromatography with DEAE cellulose, size-exclusion chromatography with Sephacryl S-300, and affinity chromatography with a specific anti-CEA antibody and then with a cross-reacting anti-CEA antibody. CEA, NCA, and Meconium Antigen (MA) were also purified by PCA extraction, mixed-bed ion-exchange chromatography equilibrated to 0.1 M ammonium acetate ($NH_4Ac$) pH 4, size-exclusion chromatography with Sepharose 6B and Sephadex G-200, and affinity chromatography with Con A Sepharose. Radiolabeled CEA was used as a marker.

Grunert, F. et al. (1984) Tumor Biology 5:221–232 teaches the use of cation-exchange chromatography to isolate CEA, but the method failed to purify CEA away from two "sticky" co-purifying proteins. The pH at which this procedure was carried out was not stated. The proteins were purified by PCA extraction, size-exclusion chromatography with Sepharose 4B and Sephadex G-150, affinity chromatography with Con A, and further purification steps chosen from: Octyl-Sepharose, DEAE-Sepharose, CM-Sepharose, Heparin-agarose, or Hydroxyapatite chromatography. The "sticky" proteins were about 45 and 58 kD.

Sheehan, D. and FitzGerald, R. (1996) Chap 14: Ion-Exchange Chromatography in "Methods in Molecular Biology: Protein Purification Protocols," Doonan, S. ed. Humana Press, New Jersey, teaches that the best approach to developing a new purification method using ion-exchange chromatography was to determine the binding of the protein of interest on both cation- and anion-exchange resins at a range of pH values. When mixed-bed ion exchange chromatography or cation-exchange chromatography was used to purify CEA family member proteins, the resulting purified proteins were not substantially free of cross-reacting antigens. When CEA family member proteins were placed in acidic solutions, sometimes they precipitated. Also, when chromatography utilizing cation-exchange resin was used, glycosylation of the protein of interest was first modified by PCA or other chemicals.

Cation-exchange chromatography was used to isolate nagase-digested CEA peptides (Banjo, C. (1974) Int. J. Cancer 13:151–163). CEA was purified by the method of Krupey, J. (1972) Immunochemistry 9:617–622 and digested with neuraminidase which decreased the carbohydrate content by over 10%, removed all of the sialic acid, and significantly reduced fucose and galactose, before digestion with nagase and cation-exchange chromatography. Chromatography was performed at pH 3.1.

Other methods known to the art have been used to purify CEA family member proteins, such as iso-electric focusing and HPLC. Hill, R. et al. (1981) Molecular Immunology 18:647–653 describes CEA purified from malignant ascitic fluid of an ovarian cancer. CEA was purified by heat treatment, PCA extraction, size-exclusion chromatography with Sephadex G150, affinity chromatography with Con A, and isoelectric focusing. Hefta, L. et al. (1992) Cancer Research 52:5647–5655 describes expression of CEA and predicted immunogenic epitopes in HeLa cells. Expressed products were purified by affinity chromatography using monoclonal antibodies specific for each domain and by reverse phase HPLC. CEA has also been purified by phosphatidlyinositol-specific phospholipase C (PI-PLC) extraction, utilizing knowledge that CEA was bound to the cell membrane by a GPI moiety (Matsuoka, Y. et al. (1991) Tumor Biology 12:91–98). Tissues were minced, homogenized, and digested with PI-PLC; size-exclusion chromatography with Sepharose 6B at pH 5.2 was performed on the supernatant. Some samples were treated with PCA before chromatography.

Many publications of new methods for purifying CEA are closely followed by further publications describing impurities of the purified products. See Rogers, G. T (1976) Biochimica et Biophysica Acta 458:355–373, Coligan, J. E. et al. (1973) Immunochemistry 10:591–599, Aitio, M. et al. (1978) FEBS Letters 93:29–32, Pusztaszeri, G. and Mach, J. (1973) Immunochemistry 10:197–204, Grunert, F. et al. (1984) Tumor Biology 5:221–232 (including PCA extraction, size-exclusion chromatography, Con A affinity chromatography, anion- and cation-exchange chromatography, heparin-agarose, and hydroxyapatite chromatography), WO 8402983 (published Aug. 2, 1984) and Ford, C. H. J. et al. (1987) Tumor Biology 8:241–250 (immuno-affinity chromatography).

Methods for purifying CEA family members have been inadequate at obtaining the protein of interest. Some of the methods, such as extraction with PCA, modified the protein of interest during the purification process. Methods for purifying individual CEA family members away from other CEA family members and other contaminants have been inadequate because so many of the proteins are physically similar. The chemical extraction and precipitation steps isolated many chemically similar proteins together. Lectin affinity steps isolated many glycosylated proteins together. Immuno-affinity steps isolated many cross-reacting antigens together. Ion-exchange chromatography isolated many similarly charged proteins together. Size-exclusion chromatography isolated many similarly sized proteins together. PI-PLC digestion isolated many GPI-membrane-bound proteins together.

None of the previously-available methods for purifying CEA family member proteins has stood out as being superior to the others. Recent applications no longer even mention a purification scheme as preferable. WO 0155337 (published Aug. 2, 2001) reports purifying a CEA-like peptide by any method known to the art.

One need in the art for pure CEA family member proteins has been for use as a vaccine. The possibility of using CEA as a vaccine has been addressed in the literature for over a decade. Attempts to use purified CEA as a vaccine have been hampered by the difficulty of obtaining sufficient quantities of sufficiently pure CEA. No method has been available for sufficiently purifying CEA, without the use of PCA, away from other cross-reacting antigens.

It has proven difficult to obtain sufficient CEA from many recombinant culture systems. High amounts of a recombinant CEA have been obtained with a baculovirus expression system. WO 95/32286 (published Nov. 30, 1995) teaches expressing CEA in insect cells using a baculovirus vector. The baculovirus CEA (bvCEA) was expressed at very high levels, secreted, and easy to purify because of its abundance and lack of physically, chemically, and immunologically related proteins. The bvCEA was used successfully as a vaccine to treat mice. WO 95/32286 (published Nov. 30, 1995) reports recombinant CEA, lacking the transmembrane domain, expressed in insect cells using a baculovirus expression system, and methods of purifying such secreted CEA. Purification methods comprise chromatography utilizing four resins: hydrophobic interaction HIC ether 650 m, HIC Butyl 650M, lentil lectin sepharose 4B, and DEAE (anion chromatography) Sepharose Fast Flow. Before chromatography, insect cell supernatant was acidified with acetic acid to pH 3.5 and incubated for one hour, in order to inactivate any virus. The supernatant was then neutralized to pH 7.0 and filtered to remove precipitated viral and cellular proteins. rCEA was said to remain soluble throughout this step. The remainder of the purification process was carried out at neutral pH. The publication also demonstrates the use of purified CEA (from Vitro Diagnostics) as a standard, for comparison of baculovirus CEA physical properties and for comparison, as a reference, of the utility of the baculovirus CEA as a vaccine.

CEA has also been cloned into a vaccinia virus vector. The vvCEA DNA vector was used directly as a vaccine. When administered to mice, it induced the generation of anti-CEA-specific T cells. Administration of vvCEA also reduced the growth of syngenic, CEA transformed, murine colon adenocarcinomas. Kaufman, H. et al. (1991) Int. J. Cancer 48:900–907 describes a recombinant Vaccinia Virus expressing CEA, and its use as a vaccine, and Kantor, J (1992) J. Nati. Cancer Inst. 84:1084–1091 describes a vvCEA vaccine. CEA was not purified. U.S. Pat. No. 5,698,530 (issued Dec. 16, 1997) reports recombinant CEA in a vaccinia virus vector, which expresses CEA on the surface of infected cells and can elicit an immune response against CEA. Methods of treating patients were included. No CEA was purified; crude lysates were used. Kass, E. et al. (1999) Cancer Research 59:676–683 describes the use of vvCEA as a vaccine in CEA-transgenic mice. The control CEA vaccine was from Vitro Diagnostics. A vvCEA vaccine has been shown to elicit an immune response in patients (Conry, R. M. et al. (1995) J. Immunother. 18:137). WO 124832 (published Apr. 12, 2001) reports CEA DNA in adenovirus and vaccinia virus vectors as pharmaceutical compositions used as vaccines to treat or prevent tumors.

These techniques have the disadvantage of including viral materials, along with CEA, in the vaccine. A vaccine uncontaminated with viral materials was preferable. Unfortunately, recent studies show that vaccines of purified CEA protein are not particularly effective. Likely this was due to the presence of CEA on normal cells, the body recognizing CEA as self, and the consequent dampening of a potential immune response. For example, when mice that express (human) CEA as a self-antigen were vaccinated with CEA protein, the CEA protein failed to elicit an immune response. However, vaccination of these mice with vvCEA elicited a strong immune response (Shlom, J. (2000) Carcinoembryonic Antigen (CEA) Peptides and Vaccines for Carcinoma in "Peptide-Based Cancer Vaccines," Kast, M. ed., Landes BioSciences). When testing vaccines of recombinant CEA family members, the corresponding native CEA family member protein was used as a reference standard (WO 95/32286 (published Nov. 30, 1995) and Kass, E. et al. (1999) Cancer Research 59:676–683).

The CEA vaccines that include viral materials, such as lysates or vectors, have been useful for demonstrating the ability of the body to mount an immune response to CEA family member proteins. Because vaccines of pure, virally uncontaminated CEA are preferable, attempts to create CEA family member protein vaccines without viral contaminants have been directed towards improving the immunogenicity of these proteins.

The immune system's ability to respond to CEA has been further demonstrated by the isolation of CEA-specific T-cells. Attention has focused on the isolation of antigens recognized by T cells because T cells are significant mediators of tumor rejection. T cells recognize antigens as epitopes that are presented on the cell surface by HLA proteins, in humans. In attempts to identify possible T cell antigen epitopes within CEA, the CEA protein sequence was searched for peptides matching the consensus motifs for HLA-A2, the most common HLA allele. Six peptide sequences, CAP1–CAP6, ranging from nine to eleven amino acids in length, were identified that matched the consensus motif for HLA-A2 and had minimal homology to the analogous sequences in the cross-reacting antigens NCA and CEACAM1-4L. A seventh peptide, CAP7, was recognized as having the motif for binding to HLA-A3. Peptides CAP1 through CAP6 were shown to bind T2 cells, with CAP1 having the strongest binding. A 177-amino-acid CEA fragment containing the CAP1 epitopes was described in EP 0343946 (published Nov. 29, 1989).

CEA T cell epitopes have been identified for a variety of HLA alleles. Thirty-four CEA specific peptides have been identified that fit with a specified HLA-A*0301-binding motif, with a set of six peptides having high binding affinity for this allele. Approximately seventy-three peptides have been identified that match the HLA-A*0201 motif. Eleven peptides have been identified that bind to HLA-A24, an allele which occurs in 60% of the Japanese population. CEA epitopes have also been identified using anti-idiotype schemes. Two such peptides are LCD-2 and CEA-B.

CEA peptides have been demonstrated to elicit CTL in vitro. Such peptides include CAP1 and CAP2 against HLA-A2, as well as peptides recognized by HLA-A3 and HLA-A24. CEA peptides have not been very effective as vaccines (Arlen, P. et al. (2000) Cancer Immunology Immunotherapy 49:517–529).

Since it was known in the art that peptide engineering can be used to alter the immunogenicity of epitopes (Kersh, G. J. and Allen, P. M. (1996) J. Exp. Med. 184:1259–1268 and Cho, B. K. (1998) J. of Immunological Methods 220:179–188), attempts to create more potent vaccines targeted to CEA have included modifying CEA epitopes. A successfully modified epitope stimulates CTL more efficiently while retaining specificity for the native antigen. Recently work has been directed toward optimizing CEA immunogenic epitopes. Because HLA-A2 was the most common HLA allele and CAP1 demonstrated the strongest binding, CAP1 was investigated (Zaremba, S. et al. (1997) Cancer Research 57:4570–4577 and WO 99/19478 (published Apr. 22, 1999)) first. These publications describe and report the CAP1peptide at amino acid positions 571–579 (YLSGANLNL, SEQ ID NO:1) and amino acid variants at positions 6 and 7, and pharmaceutical compositions containing such peptides. These modified peptides, used as a vaccine, in comparison to the native peptide, increase the immune response to CEA as demonstrated in vitro. CAP1-6D is called an agonist, because it facilitates the propagation of T-cells. Antagonists decrease the immune response to the target. Antagonist peptides are said to possibly be useful in modulating autoimmune reactions. The modified peptide CAP1-6D has the same sequence as the CAP1peptide except that it is substituted with D at the $6^{th}$ amino acid of the peptide (YLSGADLNL, SEQ ID NO:2). CAP1-6D is currently being tested as a vaccine by the N.I.H.

A control, or reference standard, in the CAP1-6D clinical trial is a native, pure CEA composition, of this invention. There is a need in the art for pure CEA, uncontaminated with cross-reacting antigens or endotoxins, not purified with PCA or antibody affinity, for use as a control or reference standard in vaccine trials (Kass, E. et al. (1999) Cancer Research 59:676–683 and WO 95/32286 (published Nov. 30, 1995). There is also a need in the art for purified CEA preparations used as calibration standards or reference antigens. For example, some assays that quantitate CEA in unknown samples utilize purified CEA as a reference. Purified CEA was utilized as a standard in the development of those assays. Purified CEA has also been used as a reference standard for analyzing physical properties (WO 95/32286, published Nov. 30, 1995) and antigenic properties (Matsuoka, Y. et al. (1991) Tumor Biology 12:91–98) of unknown samples. Labeled CEA is also useful for tracing unlabelled CEA through experiments (WO 8402983 (published Aug. 2, 1984)).

CEA-targeted vaccines are more effective with costimulatory molecule adjuvants such as the cytokine IL-2 and granulocyte-macrophage colony-stimulating factor (GM-CSF) (Shlom, J. (2000) Carcinoembryonic Antigen (CEA) Peptides and Vaccines for Carcinoma in "Peptide-Based Cancer Vaccines," Kast, M. ed., Landes BioSciences, Georgetown, Tex.). Advantages have also been noted when using diversified prime and boost strategies, for example utilizing a CEA protein vaccine and separately a CEA viral vector vaccine. Using several different CEA-targeted vaccines, individually, on the same patient, has been shown to be very effective.

Carbohydrate antigen 19-9 (CA19-9), a gastrointestinal-cancer-associated antigen, is defined by a monoclonal antibody, which was made by immunizing with a human colon cancer cell line. CA19-9 is elevated in the sera of patients with malignancies of the gastrointestinal tract, especially those who suffer from pancreatic cancer. CA19-9 is also present in normal epithelial lining of the biliary tract, gastric mucosa, pancreatic duct and bronchial glands (Obayashi, Y. et al. (2000) Respiration 67:146–152). CA19-9 has been a contaminant in CEA purifications. CA19-9 is the eptitope recognized by antibodies generated against the Sialyl Lewis A protein (Obayashi, Y. (2000) Respiration 67:146–152), such as 1116-NS-19-9 from Fujirebio Diagnostics (Japan) or NCL-CA19-9 from Novocastra Laboratories Ltd (Newcastle upon Tyne, UK).

Many proprietary purifications of CEA family member proteins are and have been available on the market, but none are as pure as the CEA family member proteins of this invention. Purity, including absence of cross-reacting antigens, CA19-9, endotoxins and antibodies, is particularly important when CEA family member proteins are used for vaccines or vaccine reference standards in trials. It is important that purification schemes not utilize antibody affinity steps, because the antibodies then appear as contaminants in the final product. It is also important that purification schemes not use perchloric acid (PCA), because PCA has been show to physically modify the glycosylation of CEA family member proteins, and such methods yield physically and immunogenically altered proteins. ERFA Biotech of Montreal, Canada, sells a CEA product that is stated to be 100% pure, purified by water homogenization, perchloric acid extraction, ion-exchange, antibody affinity and gel filtration chromatographies. This method includes use of both perchloric acid and an antibody affinity step. TriChem Resources of West Chester, Pa., also sells a CEA product, 10690B, that is stated to be at least 95% pure, purified by a method including an antibody affinity step. Lee Scientific of St. Louis, Mo., also sells CEA products, but they are purified and purchased elsewhere.

CEA has a pI of about 4.5 (U.S. Pat. No. 4,145,336 (issued Mar. 20, 1979), U.S. Pat. No. 4,140,753 (issued Feb. 20, 1979), Hill, R. (1981) Ajebak 59:469–476, and Tu, Y. Y. et al. (1988) Tumor Biology 9:212–220), has been shown to precipitate in some acidic pH ranges, and has been shown to be partially degraded by highly acidic PCA. When cation-exchange chromatography was used to purify CEA in previously known methods, two "sticky" proteins would not purify away (Grunert, F. et al. (1984) Tumor Biology 5:221–232). Mixed-bed ion-exchange, using both cation- and anion-exchange resins, was successful at isolating CEA along with a large collection of proteins and was not able to separate them from each other (U.S. Pat. No. 3,867,363 (issued Feb. 18, 1975), U.S. Pat. No. 3,956,258 (issued May 11, 1976), U.S. Pat. No. 4,086,217 (issued Apr. 25, 1978)). Newman, E. S. et al. (1974) Cancer Research 34:2125–2130 describes preparing CEA and CCA-III (NCA) using PCA extraction, mixed-bed ion-exchange chromatography at pH 4, and size-exclusion chromatography, but two forms of CEA were isolated, and the CCA-III contaminated the CEA preparation and the CEA contaminated the CCA-III preparation. WO 8402983 (published Aug. 2, 1984) describes purifying NCA and CEA using mixed-bed ion-exchange chromatography at pH 3.1, however the glycosylation-modifying chemical PCA was used, and no purity was stated except that a single band appears on gels.

SUMMARY OF THE INVENTION

This invention provides methods for purifying proteins that are selected CEA family members, including CEA, engineered CEA, CEA cross-reacting antigens, and proteins having at least about 86% amino-acid identity with CEA. Proteins are purified from many starting materials, by cation-exchange chromatography below pH 4.0 and size-exclusion chromatography. The purification methods of this invention do not utilize perchloric acid or antibody affinity steps. After purification, the proteins are of about 90% purity, substantially free of cross-reacting antigens, substantially free of CA19-9, substantially free of endotoxins and substantially free of antibodies. Preferably, after purification, the proteins are of about 90% purity, preferably at least about 95% purity, and more preferably the proteins are of at least about 98% purity, and more preferably the proteins are of about 100% purity. This invention provides the purified proteins of this invention in suitable pharmaceutical carriers, formulated for vaccines, and for use as reference standards.

DETAILED DESCRIPTION OF THE INVENTION

Figure 1:
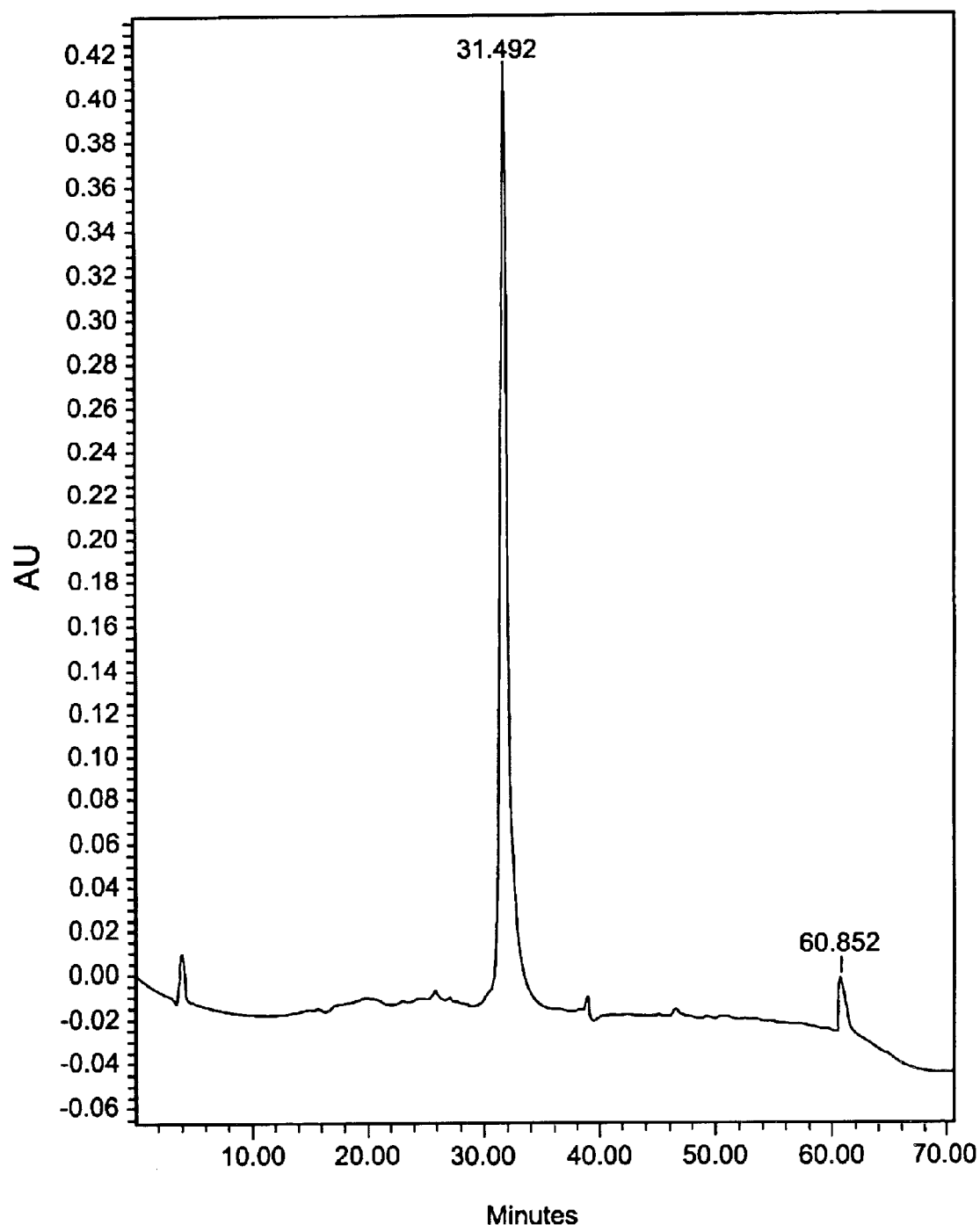
FIG. 1 Reverse phase HPLC results showing purification of about 98% purity CEA from pooled cell culture harvests.

As used herein, "substantially free of endotoxins" refers to less than about 1000 endotoxin units (EU) per mg protein.

As used herein, "substantially free of antibodies" refers to no detectable antibodies by methods known to the art.

As used herein, "endotoxin" refers to the lipopolysaccharide complex associated with the outer envelope of Gram-negative bacteria.

As used herein, "substantially free of cross-reacting antigens" refers to less than about 10% in a purified sample of the protein of interest, of molecules that are known to the art to cross-react immunologically with said protein of interest. Preferably there is less than about 5% and more preferably there is less than about 2%, and more preferably there is about 0%.

As used herein, "carcinoembryonic antigen" refers to the CEA protein, a 180 kD glycosylated protein, encoded by the CEACAM5 gene, Genbank Accession Number M17303.

As used herein, "engineered" refers to a DNA molecule or the protein encoded by that DNA molecule, that has been cloned, or is recombinant. Some engineered DNA molecules and corresponding proteins are modified by techniques known to the art, such as by recombinant DNA techniques. Engineered molecules may contain mutations such as point mutations, missense mutations, insertions, deletions, and/or rearrangements.

As used herein, "epitope" refers to the smallest peptide recognized by an antibody or T cell. Epitopes can be synthesized chemically or translated in vivo or in vitro.

As use herein, "antigen" refers to a molecule that is recognized by an antibody or T cell.

As used herein, "cross-reacting antigens" refers to two or more antigens that can be recognized by a single antibody or T cell. Cross-reacting antigens therefore share similar epitopes.

As used herein, "non-specific cross-reacting antigen" refers to the NCA protein, a glycosylated protein, which is encoded by the CEACAM6 gene (Genbank accession numbers M29541 and M18728).

As used herein, "carbohydrate antigen 19-9" refers to the epitope recognized by antibodies that recognize the Sialyl Lewis A protein.

As used herein, "AG128375" refers to the prostate-specific CEA family member cloned by AlphaGene in 2001. AG128375 refers to the gene and the corresponding protein.

As used herein, "nucleotide" refers to a single unit of deoxyribonucleic acid, DNA, or ribonucleic acid, RNA.

As used herein, "point mutation" refers to a single changed nucleotide in a sequence of DNA or RNA when compared to a reference.

As used herein, "missense mutation" refers to a point mutation that causes a change in the encoded amino acid.

As used herein, "insertion" refers to the addition of nucleotides to the interior or end of a gene causing the addition of amino acids to the encoded protein.

As used herein, "deletion" refers to the removal of nucleotides from the interior or end of a gene causing the absence of amino acids to the encoded protein.

As used herein, "immunogenicity" refers to the ability of a molecule to elicit an immune response.

As used herein, "pharmaceutical composition" refers to a composition formulated, as is known to the art, for pharmaceutical use.

As used herein, "vaccine" refers to a composition including adjuvants, that, when given to patients, may elicit an immune response.

As used herein, "ion-exchange chromatography" refers to the separation of molecules based on their charge. The ions in the mobile phase are separated by electrostatic interactions with the stationary phase.

As used herein, "cation" refers to a positively charged molecule.

As used herein, "anion" refers to a negatively charged molecule.

As used herein, "resin" refers to an insoluble solid used in chromatography.

As used herein, "anion-exchange chromatography" refers to a technique of separating selected anions from a solution using a positively charged resin.

As used herein, "cation-exchange chromatography" refers to a technique of separating selected cations from a solution using a negatively charged resin, without also using a positively charged resin.

As used herein, "mixed-bed ion-exchange chromatography" refers to a technique of separating selected anions and cations from a solution using a mixture of positively and negatively charged resins.

As used herein, "DEAE" refers to one or more diethylaminoethyl groups which when attached to a suitable resin, is a positively charged anion exchanger, useful at pH 2–9.

As used herein, "QAE" refers to one or more quaternary aminoethyl groups which when attached to a suitable resin, is a positively charged anion exchanger, useful at pH 2–12.

As used herein, "CM" refers to one or more carboxymethyl groups which when attached to a suitable resin, is a negatively charged cation exchanger, useful at pH 6–11.

As used herein, "size-exclusion chromatography" refers to a technique of separating molecules in a solution on the basis of molecular size. Gel filtration is a type of size-exclusion chromatography. A solid phase matrix consists of porous beads that are packed into a column with a mobile liquid phase flowing through the column. The mobile phase has access to both the volume inside the pores and the volume external to the beads. Larger molecules remain in the volume external to the beads, resulting in a shorter flow path, and in a more rapid exit from the column. Smaller molecules that can access the liquid within the pores of the beads are retained longer and, therefore pass more slowly through the column. The liquid leaving the column is collected in fractions. Type of resin used, size of column, and number of fractions collected are some of the variables determining which size of molecules are separated and the extent of separation from other molecules.

As used herein, the "pI" refers to the isoelectric point, the pH of equal electrical potential, of a protein.

As used herein, "solvent extraction" refers to a process of separating components of a mixture using a chemical that keeps at least the desired component in solution.

As used herein, "ethanol precipitation" refers to a method for precipitating a molecule(s) of interest by adding ethanol to a sample solution.

As used herein, "unstable" refers to a protein that is not stably dissolved in a solution and at least partially precipitates.

As used herein, "size filtration" refers to filtering a sample to exclude molecules of a certain size. Size filtration can be used to remove molecules, such as proteins, of a certain size from a sample solution, or to concentrate a sample solution by retaining a molecule and removing water. Size filtration can be used to isolate molecules of interest from a solution by first filtering out molecules smaller than the molecule of interest, and then filtering out molecules about the size of the molecule of interest, and collecting the eluent.

As used herein, "RIA" or "radio-immuno-assay" refers to immuno-affinity assay wherein the molecule(s) of interest or the antibodies are radio-labeled, and the quantitated radioactivity is utilized to quantitate the molecule(s) of interest.

As used herein, a "kit" refers to an assembled set of reagents and/or equipment, preferably packaged together.

As used herein, "purify" or "isolate" refers to separating a type of molecule from other molecules in a sample, thereby concentrating that type of molecule.

As used herein, "pure" refers to a type of molecule separated away from other types of molecules. A percentage is used to indicate the extent of purity.

As used herein, "HPLC" refers to high-pressure or high-performance liquid chromatography.

As used herein, "substantially free of cross-reacting antigens" refers to a composition of a protein of interest, said composition also comprising less than 10% of any other molecules that can be recognized by a single antibody or T cell that also recognizes the protein of interest. Preferably "substantially free of cross-reacting antigens" refers to less than 5%, more preferably less than 2%, and more preferably about 0%.

As used herein, "substantially free of NCA" refers to when the slope of the curve of the purified sample is less then two times the slope of the curve of the negative control on an NCA ELISA test, as described below.

As used herein, "substantially free of CA19-9" refers to less than 2%.

As used herein, "protein" refers to a glycosylated polypeptide.

As used herein, "peptide" refers to glycosylated, covalently-linked amino-acids, which may be a portion of a protein.

As used herein, "native" refers to a protein or DNA molecule that is identical to the corresponding protein or DNA molecule found in nature.

As used herein, "solution" refers to an aqueous solution.

As used herein, "suitable pharmaceutical carrier" refers to any formulation known in the art for delivering pharmaceuticals.

Suitable pharmaceutical carriers include carriers for vaccines. Immunogenic compositions and/or vaccines may be formulated by any of the means known in the art. They can typically be prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes. Where mucosal immunity is desired, the immunogenic compositions advantageously contain an adjuvant such as the nontoxic cholera toxin B subunit (see, e.g., U.S. Pat. No. 5,462,734). Cholera toxin B subunit is commercially available, for example, from the Sigma Chemical Company, St. Louis, Mo. Other suitable adjuvants are commercially available and may be substituted therefore. It is preferred that an adjuvant for an aerosol immunogenic (or vaccine) formulation be able to bind to epithelial cells and stimulate mucosal immunity.

Among the adjuvants suitable for mucosal administration and for stimulating mucosal immunity are organometallopolymers including linear, branched or cross-linked silicones, which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl) alkyl-terminated polydialkylsiloxanes and trialkoxysilyl-terminated polydialkylsiloxanes, for example, 3-(triethyoxysilyl) propyl-terminated polydimethylsiloxane. See U.S. Pat. No. 5,571,531, incorporated by reference herein. Phosphazene polyelectrolytes can also be incorporated into immunogenic compositions for transmucosal administration (intranasal, vaginal, rectal, respiratory system by aerosol administration) (See e.g., U.S. Pat. No. 5,562,909).

The active immunogenic ingredients are often mixed with excipients or carriers, which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol or nasal formulations is usually in the range of 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or adjuvants, which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies (especially IgG, IgM or IgA) directed against the immunogen resulting from administration of the immunogen in vaccines, which comprise the adjuvant in question. Such additional formulations and modes of administration as are known in the art may also be used.

All references cited herein are included in their entirety to the extent that they are not inconsistent with the disclosure herein.

This invention provides methods for purifying a protein, which is a selected CEA family member, including CEA, proteins having at least 86% amino-acid identity with CEA, and CEA cross-reacting antigens. Proteins are purified from many starting materials, by cation exchange chromatography below pH 4.0 and size exclusion chromatography. The purification methods of this invention do not utilize PCA or antibody affinity steps. After purification, the proteins are of at least 90% purity, substantially free of cross-reacting antigens, substantially free of CA19-9, substantially free of endotoxins, and substantially free of antibodies. Preferably after purification, the proteins are of at least 95% purity, more preferably the proteins are of at least 98% purity, and even more preferably the proteins are of at about 100% purity. This invention also provides methods for using such purified CEA family member proteins as reference standards or as pharmaceuticals, such as vaccines. This invention also provides methods for purifying engineered CEA family member proteins, such as CEA mutagenized to contain an agonistic immunogenic epitope.

It has not previously been recognized that CEA and CEA family members are stable at such low pH, that contaminants, such as protein aggregates, are unstable at such low pH, and that the method of combining the techniques used in this invention is so effective at purifying these proteins.

The methods of this invention yield CEA that is at least 90% pure and substantially free of NCA, CA19-9, endotoxins, and other cross-reacting antigens. Preferably, after purification, CEA is at least 95% pure, more preferably CEA is at least 98% pure, and more preferably CEA is about 100% pure.

The methods of this invention yield NCA that is at least 90% pure and substantially free of CEA, CA19-9, endotoxins, and other cross-reacting antigens. Preferably, after purification, NCA is at least 95% pure, more preferably NCA is at least 98% pure, and more preferably NCA is about 100% pure.

The methods of this invention yield AG128375 that is at least 90% pure and substantially free of CEA, NCA, CA19-9, endotoxins, and other cross-reacting antigens. Preferably, after purification, AG128375 is at least 95% pure, more preferably AG128375 is at least 98% pure, and more preferably AG128375 is about 100% pure.

The methods of this invention yield CAP1-6D-CEA that is at least 90% pure and substantially free of CEA, NCA, CA19-9, endotoxins, and other cross-reacting antigens. Preferably, after purification, CAP1-6D-CEA is at least 95% pure, more preferably CAP1-6D-CEA is at least 98% pure, and more preferably CAP1-6D-CEA is about 100% pure.

In one embodiment, the method of purifying a selected CEA family member to be at least 90% pure, preferably at least 95% pure, more preferably at least 98% pure, more preferably about 100% pure, and substantially free of cross-reacting antigens, CA19-9, and endotoxins comprises:

providing a starting material solution comprising a CEA family member protein, performing cation-exchange chromatography (CEC) at below pH 4 performing size-exclusion chromatography (SEC)

The chromatography steps can be performed in either order, but preferably the CEC is performed first on the provided starting material solution, and SEC is performed second using the eluent from the CEC. When the SEC is performed first, there is an equally pure but lower yield of the protein of interest.

Starting material solutions comprising CEA family member proteins can be obtained from many sources. Starting materials include: cells, tissue, fluids, and solids. Such starting materials are from cell culture or organisms, human or non-human. These cells or organisms contain a native and/or engineered CEA family member protein(s). Fluids are aqueous solutions and include cell culture aspirate and bodily fluids, such as ascites fluid. Solids include non-tissue solids such as feces.

ATCC cell lines containing CEA include: CCL-218, CCL-221, CCL-222, CCL-225, CCL-227 through CCL-231, CCL-233 through CCL-235, CCL-237, CCL-238, CCL-244, CCL-247, CCL-248, CCL-249, CCL-250, CCL-250.1, CCL-252 through CCL-255, CL-187, CL-188, CRL-1682, CRL-1687, CRL-1803, CRL-1837, CRL-1864, CRL-1918, CRL-2119, CRL-2134, CRL-2158, CRL-2159, CRL-5822, CRL-5971, CRL-5973, and CRL-5974. Two cell lines that are particularly useful in the practice of this invention are ATCC#CCL-253, designated NCI-H508, and ATCC-248, designated T84.

Starting materials can be centrifuged, such as at about 4900 g for about 30 minutes; the supernatant can comprise the starting material solution. Without wishing to be bound by any theory, the Applicants believe the centrifugation prevents the aggregation of mucins. Starting material cells can be optionally solubilized before centrifugation. Tissues and fluids are optionally homogenized and/or solubilized before centrifugation. Solubilization and homogenization are performed by methods known to the art including but not limited to using detergents, sonicators, and physical homogenizers. Starting material solutions also include samples of CEA family member proteins of less than 90% purity or not substantially free of cross-reacting antigens, CA19-9, or endotoxins. Such samples may have been partially purified by methods using PCA or antibody affinity steps. When the protein of interest is CEA, such a starting material solution may be 10695B from TriChem Resources (West Chester, Pa.), a partially purified CEA product. Starting materials are chosen such that the above methods are successful at purifying the protein of interest to at least 90%, preferably 95%, more preferably 98%, and more preferably about 100%, and substantially free of cross-reacting antigens, CA19-9, and endotoxins.

Cation-exchange chromatography used in the methods of this invention excludes the use of anion-exchange chromatography resins such as in mixed-bed ion-exchange chromatography. Cation-exchange chromatography comprises:

providing the starting material solution quantitating total protein in the starting material if not already known and if necessary, concentrating the starting material if necessary, adjusting the starting material solution to comprise CEC start buffer applying the starting material solution comprising CEC start buffer to a chromatography column packed with cation-exchange resin, preferably at least about 1 ml resin per 23 mg total protein in the adjusted starting material solution, preferably at a rate less than about 20 cm/hr washing the column with CEC start buffer until the unbound contaminating materials are washed out and the protein of interest remains bound, preferably at a rate less than about 40 cm/hr washing the column, preferably with CEC elution buffer, until the protein of interest is released, and collecting the protein of interest.

The starting material solution may be concentrated and quantitated by any method known to the art. The preferred CEC start buffer contains from 0M NaCl to about 200 mM NaCl and about 10 mM $H_3PO_4$, at below pH 4.0. Use of a pH below 4.0 decreases aggregation of some proteins. The CEC start buffer preferably contains about 0.2M NaCl when the protein of interest is CEA. The pH of the CEC start buffer varies from about pH 3.0 to below pH 4.0, and is preferably about pH 3.0 when the protein of interest is CEA. The starting material solution may be adjusted by concentrating it, dialyzing it, and adding necessary chemicals. Any cation-exchange resin known to the art to be effective between pH 2 and pH 4 may be used, such as Fractogel EM $SO_3$ (EMD $SO_3$-650 M, product No. 16882-1, CIX from EM Science, Gibbstown, N.J.). Before applying the adjusted starting material solution, the column is preferably washed with a buffer similar to the CEC start buffer, such as with 10 mM $H_3PO_4$ and 0.2M NaCl at about the pH of the CEC start buffer. The adjusted starting material solution may be applied to the chromatography column at any rate effective to provide the required purity, preferably a rate of about 20 cm/hr. The column is then washed with enough start buffer to remove substantially all the unbound proteins. The column is typically washed out with about 4 volumes of start buffer at no more than 40 cm/hr. The composition of the elution buffer is chosen such that the protein of interest is eluted with sufficiently few contaminants so that if followed by SEC, the protein of interest is at least 90% pure, preferably 95% pure and more preferably 98% pure. The CEC elution buffer preferably comprises 10 mM $H_3PO_4$ and from about 0.3M NaCl to about 1M NaCl and is at pH below 4.0. Preferably the NaCl concentration is about 1M, when the protein of interest is CEA. Preferably the pH is about 3.0. The column is typically washed with 1–2 volumes CEC elution buffer. The cation-exchange chromatography step achieves over 100-fold purification when using very low purity starting material solutions. The buffers are chosen as appropriate to obtain the required purity.

Size-exclusion chromatography comprises:

concentrating the eluent from the CEC step as necessary if necessary, adjusting the concentrated eluent to also comprise SEC buffer applying the adjusted eluent to a prepared chromatography column packed with an appropriate size-exclusion resin washing the column with SEC buffer until the protein of interest is eluted collecting the fraction(s) containing the protein of interest substantially free of contaminants The eluent from the CEC step may be concentrated by any method known to the art to between about 10 mg/ml and about 25 mg/ml. SEC buffer is any suitable buffer known to the art. The SEC buffer typically contains about 0.1M NaCl and about 10 mM $Na_2HPO_4$ at about pH 8.0. When the protein of interest is CEA, the column is preferably about 2.6 cm (diameter) by about 60 cm (length) and the resin is preferably Pharmacia Superdex 200. The column and any other glassware are typically first washed with 0.2N NaOH, a depyrogenation step that is standard to the art for preventing endotoxin contamination. The column is then typically washed with about 5 column volumes of SEC buffer at about 30 cm/hr. The size of the column, the resin used, and the number of fractions collected are modified as necessary to obtain the required purity. When a possible contaminant is of a similar size to the protein of interest, a larger column and a better-distinguishing resin are used, and more and smaller fractions are collected, as is standard in the art. The known size (kd) of the protein of interest is used to determine which fraction(s) to collect. When the protein of interest is CEA, the fractions starting at 0.25 column volumes are collected. This peak is at least 90% pure, preferably 95% pure, more preferably 98% pure, more preferably about 100% pure, and substantially free of cross-reacting antigens and endotoxins. The fraction may be concentrated by any method known to the art and is preferably lyophilized. The pellet thus produced may be resuspended in an appropriate buffer to comprise the purified sample.

These methods are effective when the starting material contains CEA family member proteins that can be obtained at the required purity by cation-exchange chromatography below pH 4.0 and size-exclusion chromatography. For the size-chromatography step, the resin, the size of the column, and the number and size of the fractions collected are chosen to obtain the required purity of the protein of interest from the selected starting material. Alternatively, a different starting material is chosen. Using larger columns, separating the eluent into more fractions, and other methods known to the art are methods that can be used to better separate similarly-sized proteins. For example, when NCA is purified by the methods of this invention, the equivalent of Sephadex G200, G150 or G100 resin is used, and the fraction containing molecules the size of NCA is collected during size-exclusion chromatography.

The percent purity of the purified sample is determined by a quantitative assay method known to the art. Typically this involves quantitating the protein of interest in the sample and quantitating the total protein in the sample.

(amount of protein of interest/amount of total protein)*100=percent purity of protein of interest Percent purity is typically determined by Reverse Phase HPLC. Reverse Phase HPLC is performed on equipment such as the Waters 2690 Alliance (Milford, Mass.) using a column such as the Zorbax® Reliance Column 300SB-C18 (Hewlett Packard, Palo Alto, Calif.) a 3.5 micron, 4.6 mm×15 cm column. To a sample to be tested, trifluoroacetic acid (TFA) is added until the sample contains 0.1% TFA. The TFA-added sample is injected onto the column. Sample Buffer, SB, containing deionized water and 0.1% TFA, is injected and the column is washed for 5 minutes. A linear gradient of SB to Elution Buffer, EB, containing 100% Acetonitrile and 0.1% TFA, is run over 60 minutes. 100% EB is held for another 5 minutes. The flow rate is 0.5 ml/min. The components of the sample are detected at a 211 nm wavelength, using a Waters PDA detector (Milford, Mass.). The output is recorded in graphical format, the curve is integrated, and the percent purity of the protein of interest is calculated.

(area under the peak for the protein of interest/area under the entire spectrum)*100=percent purity of protein of interest The possible contaminants, including cross-reacting antigens, are assayed by any means known to the art. Cross-reacting antigen levels are less than 10% total and preferably less than about 2% each. Preferably cross-reacting antigen levels are less than about 5% total, and more preferably they are less than about 2% total. Endotoxin levels are less than 1000EU but preferably less than about 100EU.

The percent purity of the protein of interest is usually determined immediately following purification.

Both CEA and NCA are collected together from the cation-exchange chromatography column. All members of the CEA gene family when matured, including glycosylated, have similar charge properties and behave similarly during cation-exchange chromatography.

The amount of CA19-9 in a sample can be quantitated with the CA19-9 Centocor® CA 19-9™ RIA system which is a solid phase radioimmunoassay. Polystyrene beads coated with 1116-NS-19-9 antibody are incubated with the specimen, standards, and controls. During this incubation, reactive determinants present in the specimen or controls are bound to the antibody on the solid phase. Unbound materials present in the specimen are removed by aspiration of the fluid and washing of the beads. The tracer, composed of $^{125}I$ labeled 1116-NS-19-9 antibody, quantifies the number of reactive determinants. Unbound labeled antibody is removed by aspiration of the fluid and washing of the beads. The bound radioactivity is proportional to the concentration of the 1116-NS-19-9 reactive determinants in the specimen within the working range of the assay. A standard curve is obtained by plotting the CA19-9 assay results of the standards vs. bound radioactivity. The CA19-9 assay results of unknowns and controls, run concurrently with the standards, can be determined from the standard curve.

The amount of NCA in a sample can be quantitated using an ELISA format comparing the unknown amount of NCA to the known amount of CEA. A 50 µl of a final concentration of 2 µg CEA/ml of the CEA test sample is loaded onto a 96-well ELISA plate and allowed to bind at 37° C. overnight. A monoclonal antibody against NCA, preferably B6.2 from NIH, is serially diluted in a range from 0.16 µg/ml to 10 µg/ml and a monoclonal antibody against CEA, preferably COL-1 from NIH, is serially diluted in a range from 0.16 µg/ml to 10 µg/ml. 50 µl of prepared B6.2 dilutions are added to half of the plate that was bound with CEA antigen, logging which dilution is added to each well. 50 µl of COL-1 dilutions are added to the second half of the plate, again logging which dilution is added to each well. The mixture is allowed to incubate at 37° C. for one hour. The plate is washed with a solution of 1% bovine serum albumin phosphate buffered saline. An appropriate dilution of Horseradish Peroxidase-labeled anti-mouse secondary antibody is prepared. 50 µl is added to the plate and allowed to incubate for one hour at 37° C. The plates are once again washed, and 100 µl of the colorimetric detection reagents A and B were added to each well, and the plate was allowed to incubate for 5–15 minutes at room temperature. A 1N $H_2SO_4$ stop reagent is added to each well, and the absorbance is read at 450 nm. The NCA result is determined by calculating the slope of the curve of the plotted absorbances at 450 nm. A sample is substantially free of NCA when the slope of the line formed by plotting the antibody concentration versus the absorbance, is less than double the slope of the negative control line.

The amount of endotoxins in a sample can be quantitated with the Quantitative Chromogenic Limulus Amebocyte Lysate (LAL), QCL-1000®, test kit, catalog number 50-648U, license number 709, from BioWhittaker, a CAMBREX company. This assay utilizes a modified LAL and a synthetic color producing substrate to detect endotoxin chromogenically. The Chromogenic LAL test is a quantitative test for gram-negative bacterial endotoxin. A sample is mixed with the LAL supplied in the test kit and incubated at 37° C. for six minutes. The reaction is stopped with stop reagent. If endotoxin is present in the sample a yellow color will develop. The absorbance of the sample is determined spectrophotometrically at 405–410 nm. Since this absorbance is in direct proportion to the amount of endotoxin present, the concentration of endotoxin is calculated from a standard curve. If the concentration of endotoxin in the test sample is greater than 1 EU/ml, the sample is diluted 5-fold and retested.

The amount of CEA in a sample can be quantitated by assaying with an analyzer such as the ACS 180 Analyzer from Bayer (ACS:180 SE, Tarrytown, N.Y.) or the IMX analyzer from Abbott (AXSYM, Abbott Park, Ill.) that quantitates the amount of CEA in a sample. The Bayer analyzer works in a cuvette by binding the CEA in the sample with rabbit polyclonal anti-CEA antibodies that are labeled with a chemiluminescent reaction component and a mouse monoclonal antibody coupled to magnetic particles. The cuvette is washed while the bound CEA is magnetically retained. Additional reagents are added to initiate the chemiluminescent reaction, which is measured. The amount of chemiluminescence is proportional to the amount of CEA in the sample. The Abbott IMX analyzer assay is based on Microparticle Enzyme Immunoassay technology. The sample is mixed with microparticles coated with mouse monoclonal anti-CEA, and an aliquot is placed on a glass fiber matrix. The microparticles bind to the glass fiber matrix, along with the bound CEA. The matrix is washed. Mouse monoclonal anti-CEA that is bound to alkaline phosphatase is added, it binds to the CEA, and the excess is washed off. The substrate, 4-methylumbelliferyl phosphate, is added and the product of the reaction is quantitated by an optical assembly. The measurement is proportional to the amount of CEA in the original sample.

The methods of this invention are useful for purifying CEA proteins, including, native and engineered CEA family members. An example of an engineered CEA is the CEA minigene containing only the N-A3 domains (You, Y. H. (1998) Anticancer Research 18:3193–3202). The methods of this invention are useful for purifying the N-A3 CEA minigene.

The compositions of this invention are usefull for research and for the diagnosis, prognosis, and treatment of diseases. The compositions of this invention are useful as individual reagents or as components in kits, such as those supplied with 180 analyzers. The compositions of this invention are useful as antigens for making polyclonal and monoclonal antibodies. The compositions of this invention are useful as standards or references such as for testing physical properties of other compositions (WO 95/32286, published Nov. 30, 1995) or as a marker in assays (WO 8402983, published Aug. 2, 1984; U.S. Pat. No. 4,299,815, issued Nov. 10, 1981). In diagnosis and prognosis, compositions of this invention can be used as reference standards, against which a patient's level of the corresponding protein(s) is compared. The compositions of this invention can be used as control vaccines, reference standards against which potentially more effective vaccines are compared (Kass, E. et al. (1999) Cancer Research 59:676–683). Using a composition of this invention as a vaccine reference standard to test a sample vaccine comprises: providing a first sample vaccine, providing a purified composition of this invention formulated as a second vaccine, vaccinating a first subject with said first sample vaccine, vaccinating a second subject with said second reference standard vaccine, and comparing the level of immune response provided by said first sample vaccine and to the level of immune response provided by said second vaccine. A composition of this invention is also useful as a vaccine reference standard when the sample vaccine comprises a composition of this invention.

Currently the N.I.H. is conducting a vaccine trial of the CEA-derived agonist peptide CAP1-6D. As a control against which to compare its effectiveness, a purified CEA composition of this invention, purified by-the methods of this invention, is also being used to vaccinate patients. This invention also provides a vaccine that is even more effective than the CAP1-6D peptide vaccine comprising the CAP1-6D epitope in an engineered CEA protein, made by methods standard to the art comprising: engineering a DNA sequence encoding the CAP1-6D peptide (at amino acid 576, N D) into a full-length CEACAM5 gene, expressing this engineered CAP1-6D-CEACAM5 gene in cells (that don't contain native CEA protein) that provide appropriate maturation including glycosylation, and purifying corresponding CAP1-6D-CEA by the methods of this invention. A vaccine comprising CAP1-6D-CEA may comprise all appropriate adjuvants, as described above, and maybe given in an appropriate prime/boost cycle, as is known to the art. This invention provides a CAP1-6D-CEA vaccine, comprising a composition of this invention, purified by the methods of this invention.

This invention also uses the CAP1-6D-CEA composition of this invention as a control, or reference standard, for comparing the effectiveness of other vaccines. This invention also provides examples of other vaccines comprising, for example: CEA containing other agonistically engineered epitopes. Such CEA compositions may contain: other agonistic modifications of CAP1; agonistic modifications of other epitopes, such as CAP2–CAP6 recognized by HLA-A2, CAP7 recognized by HLA-A3, LCD-2 and CEA-B recognized by HLA-A24, epitopes recognized by HLA-A*0301, HLA-A*0201, and other epitopes recognized by the immune system; agonistic modifications at more than one of these epitopes in each CEA molecule; one or more of the above-mentioned agonistic epitopes inserted into or fused onto the CEA molecule, possibly within the context of an additional domain; or proteins comprising deletions in CEA, such as deletions of particular domains, with one of the remaining domains containing one or more of the above-mentioned agonistic epitopes; of which all vaccines comprise compositions of this invention, purified by the methods of this invention.

This invention also provides other CEA family members that are engineered to contain agonistic epitopes, the compositions of this invention comprising such engineered CEA family members, the purification of such compositions by the methods of this invention, and the use of such compositions as vaccines. This invention also provides the use of such compositions comprising native CEA family members as controls or reference standards against which to compare the effectiveness of such vaccines.

This invention provides vaccines, comprising one or more compositions of this invention. A vaccine comprising two engineered CEA compositions of this invention, each modified at a different immunogenic epitope, such as CAP1-6D-CEA and a CEA agonistically-engineered at an HLA-A24 epitope, both purified by the methods of this inventions, is an example of such a vaccine. This invention also contemplates more than one vaccine, each containing at least one composition of this invention, utilized sequentially in varying prime and boost strategies. This invention also provides purifying CEA family members engineered to contain antagonistic epitopes.

This invention provides compositions comprising purified CEA family-members, native and engineered, from other species, such as those found in primates, guinea pigs, rats, and mice. The methods of this invention are useful for purifying such CEA family member proteins.

The methods of this invention are useful for purifying proteins of the CEA family that are present in the starting material solutions only containing other CEA family member proteins that are separable by size-exclusion chromatography. For example, the methods of this invention are not useful for purifying CAP1-6D-CEA from a cell line that expresses native CEA, for these products are essentially identical in size and not practically separable by size-exclusion chromatography. The methods of this invention are useful if it is desirable to purify both proteins together, such that the composition comprising both proteins is at least about 90% pure, preferably at least about 95% pure and more preferably at least about 98% pure. The methods of this invention are useful for purifying CAP1-6D-CEA from a cell line that does not express native CEA, including but not limited to such starting materials as a CAP1-6D-CEA transformed mouse cell line. Similarly, the methods of this invention are useful for purifying AG128375 and engineered AG128375 containing agonistic immunogenic epitopes.

Purified compositions of at least about 90% purity, preferably of at least about 95% purity and more preferably at least about 98% purity, of proteins having at least about 86% amino acid identity with CEA include, but are not limited to, NCA. Both CEA and NCA are cleaved of an N-terminal signal peptide of about 34-amino-acids and a C-terminal peptide, that possibly directs membrane attachment, of about 26 amino acids. Before these peptides are cleaved, CEA and NCA are about 84% identical. Methods for determining amino acid sequence identity are known to the art. CAP1-6D-CEA is 99.8% identical to CEA. The N-A3 minigene is 100% identical.

All references cited in the present application are incorporated in their entirety herein by reference to the extent not inconsistent herewith.

It will be appreciated by those of ordinary skill in the art that starting materials, CEA family member proteins, and purification methods other than those specifically disclosed herein are available in the art and can be employed in the practice of this invention. All art-known functional equivalents of starting materials, CEA family member proteins, and purification methods are intended to be encompassed in this invention.

The following examples are provided for illustrative purposes only, and are not intended to limit the scope of the invention as claimed herein. Any variations in the exemplified articles which occur to the skilled artisan are intended to fall within the scope of the present invention.

EXAMPLE 1

CEA Purification from Human Liver Tissue 1

30.6 g of lyophilized human liver tissue, including tumor tissue, were extracted for CEA at a neutral pH and the sample was brought to a concentration of 0.1M sodium chloride and adjusted to pH 3.0. The CEA containing sample was then applied to Fractogel EM $SO_3$ cation exchange chromatography media equilibrated to pH 3.0 with 10 mM glycine and 0.1M sodium chloride, pH 3.0. The total protein of the sample was 29820 mg and the column volume was 1250 ml giving a load of 23.9 mg total protein per milliliter of packing material. The column was washed with the equilibration buffer to wash out all of the non-absorbed protein. The CEA was then eluted with a linear gradient to buffer B: 10 mM glycine, 0.5M sodium chloride, pH 3.0. The CEA eluted at about 0.25M sodium chloride, and the CEA content was determined using Bayer's ACS-180 analyzer.

The CEA-containing fraction was concentrated to 10–15 mg/ml total protein in a YM-30 stirred cell concentrator. The 8.0 ml sample was injected onto a Pharmacia Superdex 200 size-exclusion chromatography column with a diameter of 2.6 cm and a length of 60 cm. The CEA was eluted in 20 mM tris, 0.75M sodium chloride, pH 7.5. A single band appeared on SDS-PAGE.

EXAMPLE 2

CEA Purification from Pooled Cell Culture Harvests 1

Two CEA-containing human tumor cell lines, ATCC #CCL-253 and ATCC #CCL-248, were grown for four weeks. Spent media was then collected daily.

Cell culture spent media containing CEA from both cell lines was harvested, pooled, centrifuged, concentrated in a 30 kDa filter and dialyzed into a low conductivity neutral pH buffer. The sample was then injected onto the cation-exchange chromatography column and eluted as described above at a protein load of 20.8 mg/ml. The CEA was eluted at about 0.25M sodium chloride to a purity of approximately 2.5%.

The CEA-containing fractions were pooled and the sample was concentrated to 30 mg/ml total protein. As described above, the sample was injected onto a size-exclusion chromatography column and eluted at a purity of about 98% percent, as determined by reverse phase HPLC, as shown on FIG. 1. A single band appeared on SDS-PAGE.

EXAMPLE 3

CEA Purification from TriChem Resources Partially Purified CEA

Partially purified CEA, product #10695B (lot #01H0801FP) was received from TriChem Resources. The sample was centrifuged, concentrated using a 30 kDa hollow fiber cartridge, and injected onto the Superdex 200 SEC column. The fractions coming off the column were pooled, labeled A-G and assayed. The purity of the CEA did not meet requirements, therefore the B fraction was concentrated a second time and reprocessed by injecting it onto the SEC column again, to achieve a higher purity CEA. The sample still did not meet percent purity standards. All of the CEA that was eluted from the two SEC runs was pooled and injected onto the a CIX (Fractogel EM $SO_3$ EMD $SO_3$-650 M, product No. 16882-1, CIX from EM Science, Gibbstown, N.J.) containing CEC column. Fractions 8 and 9 were pooled to obtain 100% of the CEA injected onto the column. The purity was determined to be 100% by reverse phase HPLC. Contaminants were measured to be: CA19-9= less then 0.31% and less than 0.2 mg/mg total protein using Centocor® CA 19-9™ RIA, NCA=negative using enzyme immunoassay, and endotoxin=468 EU/mg total protein using BioWhittaker LAL QCL-1000 (Cambrex, East Rutherford, N.J.). The sample was finally processed by concentrating the sample in a 30 kDa filter and diafiltering into PBS. A final pre-bottle assay was performed and the contaminants measured. An SDS-PAGE gel showed the CEA band present near the top of the gel without any contaminating bands.

EXAMPLE 4

Purification of CEA from Liver Tissue 2

Approximately 5.0 g of lyophilized human liver tissue, including tumor tissue, was extracted with a PBS buffer at pH 7.5 to obtain an 80 ml starting material solution containing 5292.8 mg total protein with only 0.2 mg of CEA. 25 ml of the sample was injected onto a column containing 90 ml Fractogel EM sulfate cation exchange chromatography media equilibrated in start buffer: 10 mM $H_3PO_4$, 200 mM NaCl at pH 3.0. The total protein load on the column was 18.3 mg/ml with a CEA load of 0.063 mg total. The unbound proteins were washed with start buffer for 4 column volumes and the CEA was eluted in a gradient to elution buffer: 1.0M NaCl, 10 mM $H_3PO_4$ PH 3.0 over 3-column-volumes. The small amount of CEA was then concentrated and injected onto a column containing Pharmacia Superdex 200. A purified peak of CEA was eluted, as observed by HPLC.

EXAMPLE 5

Purification of CEA from Cell Culture Media

An ATCC #CCL-253, NCI H508, cell culture was harvested and the one-day harvest centrifuged, concentrated, and diafiltered into a low conductivity neutral pH buffer. The sample was adjusted to pH 3.0 and injected onto a column containing 90 ml Fractogel EM sulfate cation exchange chromatography media equilibrated in start buffer: 10 mM $H_3PO_4$, 200 mM NaCl at pH 3.0. The total protein load was 1.7 mg/ml and the CEA load was 1.35 mg total. The non-absorbed proteins were washed with 4 column volumes of start buffer and CEA was eluted in a 3-column-volume gradient to elution buffer. The CEA eluted at approximately 25% of the gradient at a purity of 66%. The CEA fraction was concentrated to 2.2 ml and 0.816 mg total protein, and injected onto a 16 cm/60 cm column containing 120 ml of Superdex 200 resin. The CEA was eluted at 30 cm/hr in eluent: 10 mM sodium phosphate and 0.1 M sodium chloride pH 8.0. The 1.1 mg of CEA was determined to be greater than 98% pure by reverse phase HPLC and SDS PAGE.

EXAMPLE 6

Purification of CEA from Partially Purified Ascites Fluid

Figure 2:
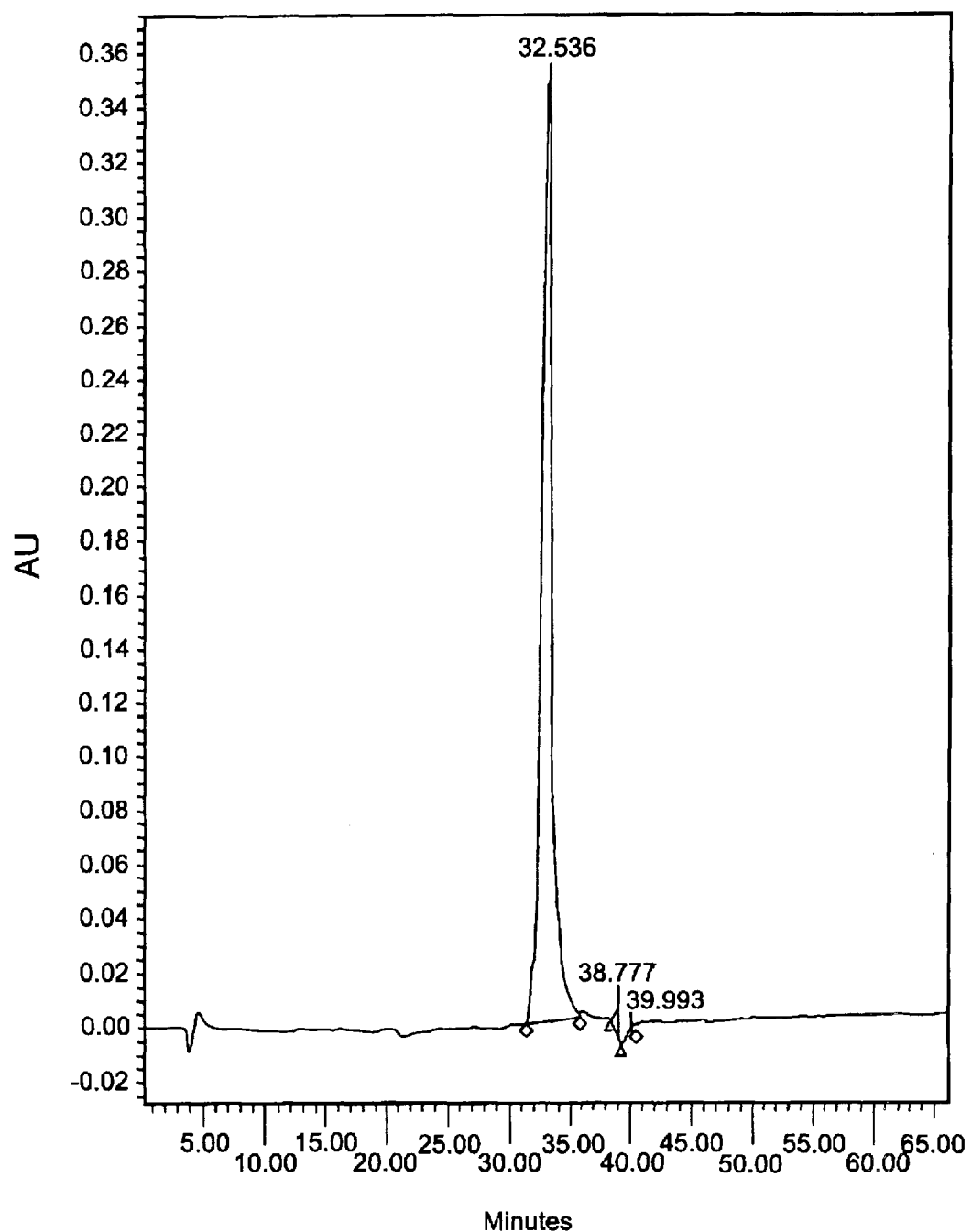
FIG. 2 Reverse phase HPLC results showing purification of about 99% purity CEA from partially purified ascites fluid.

Partially purified CEA was obtained from Tri-Chem Resources (West Chester, Pa., product code 10695B, lot #05J2601FP). The fluid was adjusted to pH 3.0 and injected onto the column containing 90 ml Fractogel EM sulfate cation exchange chromatography media equilibrated in start buffer: 10 nM $H_3PO_4$, 200 mM NaCl at pH 3.0. The non-absorbed protein was washed off the column with 4 volumes of start buffer, and the CEA was eluted with a 3-column-volume gradient to elution buffer. The CEA was eluted at 37% purity. The CEA containing fractions were concentrated to 11.6 mg/ml total protein and injected onto a 2.6 cm/100 cm column containing Superdex 200 resin equilibrated in eluent. The CEA-containing fractions were concentrated and injected onto the SEC column a second time as a polishing step and to determine purity. As shown on FIG. 2, the sample was eluted and determined to be of about 99% purity by SDS-PAGE and reverse phase HPLC.

EXAMPLE 7

Purification of CEA from Pooled Cell Culture Harvests 2

Two cell culture harvests were pooled, centrifuged, concentrated, and diafiltered in low conductivity, neutral pH buffer. The sample contained 9571 mg total protein and 17 mg CEA. The sample was brought to 0.2M NaCl, adjusted to pH 3.0, and injected onto a column containing 600 ml Fractogel EM sulfate resin. The total protein load was 15.95 mg/ml. The non-absorbed proteins were washed with 4 volumes of start buffer, and the CEA was eluted in a 3-column-volume gradient to 100% elution buffer. The CEA eluted at a purity of approximately 10%. The CEA-containing fractions were concentrated to 16 ml, and injected onto a Superdex 200 column and eluted with eluent. The sample was collected, pooled, and injected onto the SEC column as a polishing step to determine purity. The sample was determined to be greater than 98% pure by SDS-PAGE and reverse phase HPLC.

EXAMPLE 8

Reverse Phase HPLC of TriChem Resources CEA product, 10690B

Figure 3:
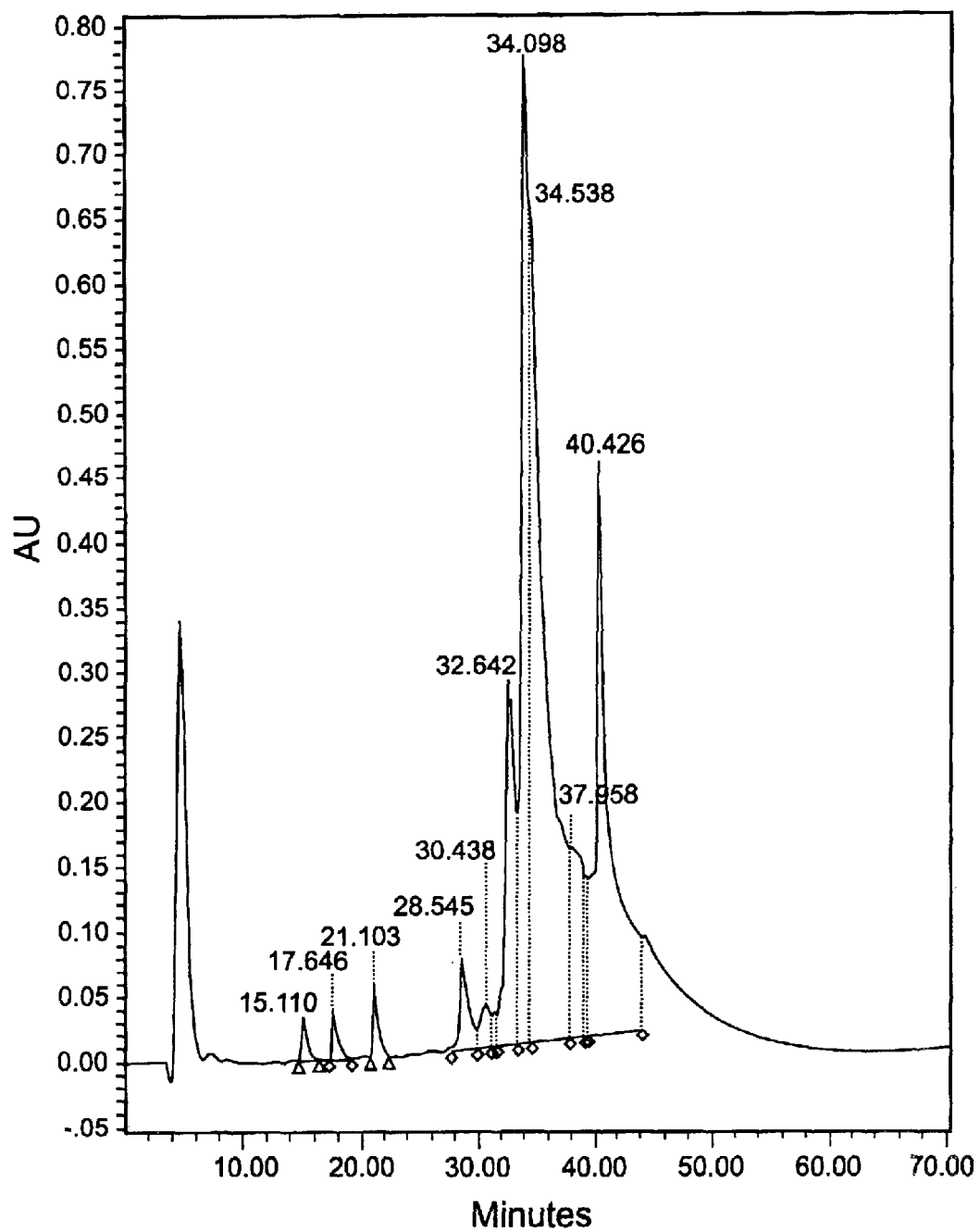
FIG. 3 Reverse Phase HPLC results of TriChem Resources CEA product, 10690B, showing a purity of about 50%.

A sample of TriChem Resources (West Chester, Pa.) CEA product, 10690B, was tested for purity by reverse phase HPLC. TriChem Resources' literature suggests their product is 95% pure, however our testing by reverse phase HPLC demonstrated this product to only be of about 50% purity, as shown in FIG. 3. About ten peaks were detected.

What is claimed is:

1. A method for purifying a protein wherein after purification said protein is of at least 90% purity, is substantially free of cross-reacting antigens and antibodies, and is selected from the group consisting of: proteins having at least about 86% amino acid identity with CEA; proteins that immunologically cross-react with CEA; and proteins encoded by a gene selected from the group consisting of CEACAM1, CEACAM2, CEACAM3, CEACAM4, CEACAM5, CEACAM6, CEACAM7, CEACAM8, AG128375, PSG1, PSG2, PSG3, PSG4, PSG5, PSG6, PSG7, PSG8, PSG9, PSG10, PSG11, CEACAM-ps1, CEACAM-ps2, CEACAM-ps3, CEACAM-ps4, CEACAM-ps5, CEACAM-ps6, CEACAM-ps7, CEACAM-ps8, CEACAM-ps9, CEACAM-ps10, and CEACAM-ps11; said method comprising:

(a) providing a starting material solution comprising said protein;

(b) performing cation-exchange chromatography (CEC) below pH 4 on said starting material solution; and (c) performing size-exclusion chromatography (SEC), wherein said method does not comprise use of perchloric acid.

2. The method of claim 1 not including use of an antibody affinity step.

3. The method of claim 1 wherein the CEC is performed below pH 3.1.

4. The method of claim 1 wherein the CEC is performed at about pH 3.0.

5. The method of claim 1 wherein said cation-exchange chromatography is performed before said size-exclusion chromatography.

6. The method of claim 1 preceded by steps comprising (a) providing a starting material comprising said protein; and (b) solubilizing said starting material to form a starting material solution.

7. The method of claim 6 wherein the starting material is selected from the group consisting of human liver tissue and human tumor cell lines.

8. The method of claim 1 wherein the starting material solution is selected from the group consisting of ascites fluid, partially purified solutions, and spent media.

9. The method of claim 7 wherein the human tumor cell line is selected from the group consisting of ATCC #CCL-253 and ATCC #CCL-248.

10. The method of claim 1 yielding a protein which is at least 95% pure.

11. The method of claim 1 yielding a protein which is at least 98% pure.

12. The method of claim 1 wherein said protein immunologically cross-reacts with CEA.

13. The method of claim 1 wherein said protein has at least about 86% amino acid identity with CEA.

14. The method of claim 1 wherein after purification said protein is substantially free of cross-reacting antigen NCA.

15. The method of claim 1 wherein said protein is CEA.

16. A method for purifying a protein comprising a peptide having the amino acid sequence of SEQ ID NO:2 comprising (a) providing a starting material solution comprising said protein;

(b) performing cation-exchange chromatography (CEC) below pH 4 on said starting material solution; and (c) performing size-exclusion chromatography (SEC), wherein said method does not comprise use of perchloric acid.

17. The method of claim 1 yielding a protein which is 100% pure.

18. The method of claim 1 wherein after purification said protein is substantially free of CA19-9.

19. The method of claim 1 wherein after purification said protein is substantially free of endotoxins.

20. The method of claim 1 wherein said protein is encoded by a gene selected from the group consisting of CEACAM1, CEACAM2, CEACAM3, CEACAM4, CEACAM5, CEACAM6, CEACAM7, CEACAM8, PSG1, PSG2, PSG3, PSG4, PSG5, PSG6, PSG7, PSG8, PSG9, PSG10, PSG11, CEACAM-ps1, CEACAM-ps2, CEACAM-ps3, CEACAM-ps4, CEACAM-ps5, CEACAM-ps6, CEACAM-ps7, CEACAM-ps8, CEACAM-ps9, CEACAM-ps10, and CEACAM-ps11.

21. The method of claim 1 wherein said protein is encoded by a gene selected from the group consisting of CEACAM1, CEACAM3, CEACAM4, CEACAM5, CEACAM6, CEACAM7, CEACAM8, PSG1, PSG2, PSG3, PSG4, PSG5, PSG6, PSG7, PSG8, PSG9, PSG10, PSG11, CEACAM-ps1, CEACAM-ps2, CEACAM-ps3, CEACAM-ps4, CEACAM-ps5, CEACAM-ps6, CEACAM-ps7, CEACAM-ps8, CEACAM-ps9, CEACAM-ps10, and CEACAM-ps11.

22. The method of claim 1 wherein said protein is encoded by a gene selected from the group consisting of CEACAM1, CEACAM3, CEACAM4, CEACAM5, CEACAM6, CEACAM7, CEACAM8, PSG1, PSG2, PSG3, PSG4, PSG5, PSG6, PSG7, PSG8, PSG9, PSG10, and PSG11.

23. The method of claim 1 wherein said protein is encoded by a gene selected from the group consisting of CEACAM1, CEACAM3, CEACAM4, CEACAM5, CEACAM6, CEACAM7, CEACAM8.

24. The method of claim 1 wherein said protein is encoded by a gene selected from the group consisting of CEACAM5 and CEACAM6.

* * * * *